(12) United States Patent
Priyankara et al.

(10) Patent No.: US 10,912,464 B2
(45) Date of Patent: Feb. 9, 2021

(54) SYSTEM AND METHOD FOR MONITORING VASCULAR SYSTEM HEALTH

(71) Applicant: JENDO INNOVATIONS (PVT) LTD, Piliyandala (LK)

(72) Inventors: Mahawaththa Kodithuwakkuge Keerthi Priyankara, Matara (LK); Wijesekara Vithanage Charith, Matara (LK); Mundigala Arachchillage Isuru Suharshan Rajakaruna, Eheliyagoda (LK)

( * ) Notice: Subject to any disclaimer, the term of this patent is extended or adjusted under 35 U.S.C. 154(b) by 92 days.

(21) Appl. No.: 16/089,405

(22) PCT Filed: Mar. 27, 2017

(86) PCT No.: PCT/SG2017/050155
§ 371 (c)(1),
(2) Date: Sep. 28, 2018

(87) PCT Pub. No.: WO2017/171637
PCT Pub. Date: Oct. 5, 2017

(65) Prior Publication Data
US 2019/0380592 A1 Dec. 19, 2019

(30) Foreign Application Priority Data
Mar. 28, 2016 (LK) .......................................... 18722

(51) Int. Cl.
*A61B 5/02* (2006.01)
*A61B 5/01* (2006.01)
(Continued)

(52) U.S. Cl.
CPC ............ *A61B 5/02007* (2013.01); *A61B 5/01* (2013.01); *A61B 5/02055* (2013.01);
(Continued)

(58) Field of Classification Search
CPC ... A61B 5/02007; A61B 5/01; A61B 5/02055; A61B 5/0402; A61B 5/14551;
(Continued)

(56) References Cited

U.S. PATENT DOCUMENTS

| 6,356,774 B1 | 3/2002 | Bernstein et al. |
| 2009/0163787 A1* | 6/2009 | Mannheimer ........ A61B 5/4875 600/324 |

(Continued)

FOREIGN PATENT DOCUMENTS

WO 2017/008138 A1 1/2017

OTHER PUBLICATIONS

Bo et al "The research of electrophysiological data normalization" The 5th International Conference on Computer Science & Education Hefei, China, Aug. 24-27, 2010 (Year: 2010).*
(Continued)

*Primary Examiner* — Catherine M Voorhees
*Assistant Examiner* — Roland Dinga
(74) *Attorney, Agent, or Firm* — Egbert, McDaniel & Swartz, PLLC

(57) ABSTRACT

The present disclosure generally relates to a system and method for non-invasively monitoring health of a vascular system of a patient. The system comprises a monitoring device for measuring vascular activity of the patient; and a server configured for performing steps of the method. The method steps comprise: receiving a set of signals comprising a vascular signal derived from vascular activity measurements of the patient by the monitoring device; reconstructing an identity pulse from the vascular signal; determining identity pulse features from the identity pulse; comparing data from a set of features with a patient database, the set of features comprising the identity pulse features; and generating a patient risk assessment of vascular health conditions (Continued)

based on results from the comparison with the patient database, wherein the patient database comprises data associated with the set of features for a population of patients.

17 Claims, 15 Drawing Sheets

(51) Int. Cl.
*A61B 5/0205* (2006.01)
*A61B 5/0402* (2006.01)
*A61B 5/1455* (2006.01)
*A61B 5/00* (2006.01)
*A61B 5/024* (2006.01)

(52) U.S. Cl.
CPC ........ *A61B 5/0402* (2013.01); *A61B 5/14551* (2013.01); *A61B 5/7203* (2013.01); *A61B 5/7275* (2013.01); *A61B 5/024* (2013.01); *A61B 5/02416* (2013.01)

(58) Field of Classification Search
CPC ..... A61B 5/7203; A61B 5/7275; A61B 5/024; A61B 5/02416
See application file for complete search history.

(56) References Cited

U.S. PATENT DOCUMENTS

| | | |
|---|---|---|
| 2011/0152638 A1 | 6/2011 | Bartnik et al. |
| 2014/0135633 A1* | 5/2014 | Anderson .............. A61B 5/026 600/486 |
| 2015/0335228 A1 | 11/2015 | Lei et al. |
| 2015/0339442 A1 | 11/2015 | Oleynik |

OTHER PUBLICATIONS

Roonizi et al "Morphological modeling of cardiac signals based on signal decomposition" computer in biology and medicine 43(2013) 1453-1461 (Year: 2013).*

* cited by examiner

SYSTEM AND METHOD FOR MONITORING VASCULAR SYSTEM HEALTH

CROSS REFERENCE TO RELATED APPLICATIONS

The present disclosure claims the benefit of Sri Lanka Patent Application No. 18722 filed on 28 Mar. 2016, which is incorporated in its entirety by reference herein.

TECHNICAL FIELD

The present disclosure generally relates to a system and method for monitoring vascular system health. More particularly, the present disclosure describes various embodiments of a system and method for non-invasively monitoring health of one or more vascular systems of a patient, such as the peripheral vascular system and cardiac vasculature system.

BACKGROUND

The vascular system, also called the circulatory or cardiovascular system, is an organ system made up of blood vessels (arteries, veins, and capillaries) that carry and circulate blood throughout the human body. Through this blood circulation, oxygen and nutrients (e.g. amino acids and electrolytes) are delivered to the body tissues, and tissue waste matter is removed. A healthy vascular system with good blood circulation is important to provide nourishment and help in fighting diseases, stabilize temperature, and maintain homeostasis in the body. The vascular system includes the peripheral vascular system which relates to blood circulation in the arteries and veins that are not in the chest or abdomen (i.e. in the limbs and extremities), as well as the cardiac vasculature system which relates to the cardiac function of the heart.

Epithelium or epithelial tissues line the cavities and surfaces of blood vessels and organs throughout the body. Vascular endothelium is a type of epithelium that lines the vascular system, from the heart to the blood vessels in the body. The vascular endothelium or endothelial cells line the interior surface of blood vessels to form an interface between circulating blood in the blood vessel lumens and the rest of the blood vessel walls.

The vascular endothelium is a highly active monolayer of endothelial cells which plays a key role in maintaining vascular homeostasis. Endothelial dysfunction is a systemic pathological state of the endothelium, which is known as the indication of early stage formation of atherosclerosis (also known as arteriosclerotic vascular disease or ASVD). Atherosclerosis is a disease in which plaque forms and builds up inside the arteries. The hardening and narrowing of the arteries eventually blocks them and limits flow of oxygen-rich blood to organs and other parts of the body.

Studies have shown a correlation between endothelial dysfunction and diseases in the vascular system. An early diagnosis on the endothelial dysfunction may lead to early identification of vascular health conditions or diseases. Although there are some existing methods of assessing or measuring endothelial function, some are invasive to the patient, such as by measuring oxygen saturation directly through a blood sample.

Therefore, in order to address or alleviate at least one of the aforementioned problems and/or disadvantages, there is a need to provide a system and method for non-invasively monitoring health of a vascular system of a patient, in which there is at least one improvement and/or advantage over the prior art.

SUMMARY

According to an aspect of the present disclosure, there is a system, a method, and a non-transitory computer medium for non-invasively monitoring health of a vascular system of a patient. The system comprises a monitoring device for measuring vascular activity of the patient; and a server configured for performing steps of the method. The method steps comprise: receiving a set of signals comprising a vascular signal derived from vascular activity measurements of the patient by the monitoring device; reconstructing an identity pulse from the vascular signal; determining identity pulse features from the identity pulse; comparing data from a set of features with a patient database, the set of features comprising the identity pulse features; and generating a patient risk assessment of vascular health conditions based on results from the comparison with the patient database, wherein the patient database comprises data associated with the set of features for a population of patients.

An advantage of the present disclosure is that by reconstructing and using an identity pulse for comparison, there is a more standardized approach which patients, clinics, medical facilities, etc. can adopt to assess risks of vascular health conditions. Compared to a conventional signal or pulse train, a single identity pulse derived in substantially the same manner for different patients can more effectively emphasize the variations between patients depending on their vascular health, resulting in better accuracy in detecting/predicting vascular health conditions/anomalies/diseases.

A system and method for non-invasively monitoring health of a vascular system of a patient according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. As used herein, the term "set" corresponds to or is defined as a non-empty finite organization of elements that mathematically exhibits a cardinality of at least one (e.g. a set as defined herein can correspond to a unit, singlet, or single element set, or a multiple element set), in accordance with known mathematical definitions. The recitation of a particular numerical value or value range herein is understood to include or be a recitation of an approximate numerical value or value range.

For purposes of brevity and clarity, descriptions of embodiments of the present disclosure are directed to a system and method for non-invasively monitoring health of a vascular system of a patient, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, known systems, methods, procedures, and components have not been described in detail so as to not unnecessarily obscure aspects of the embodiments of the present disclosure.

Figure 1:
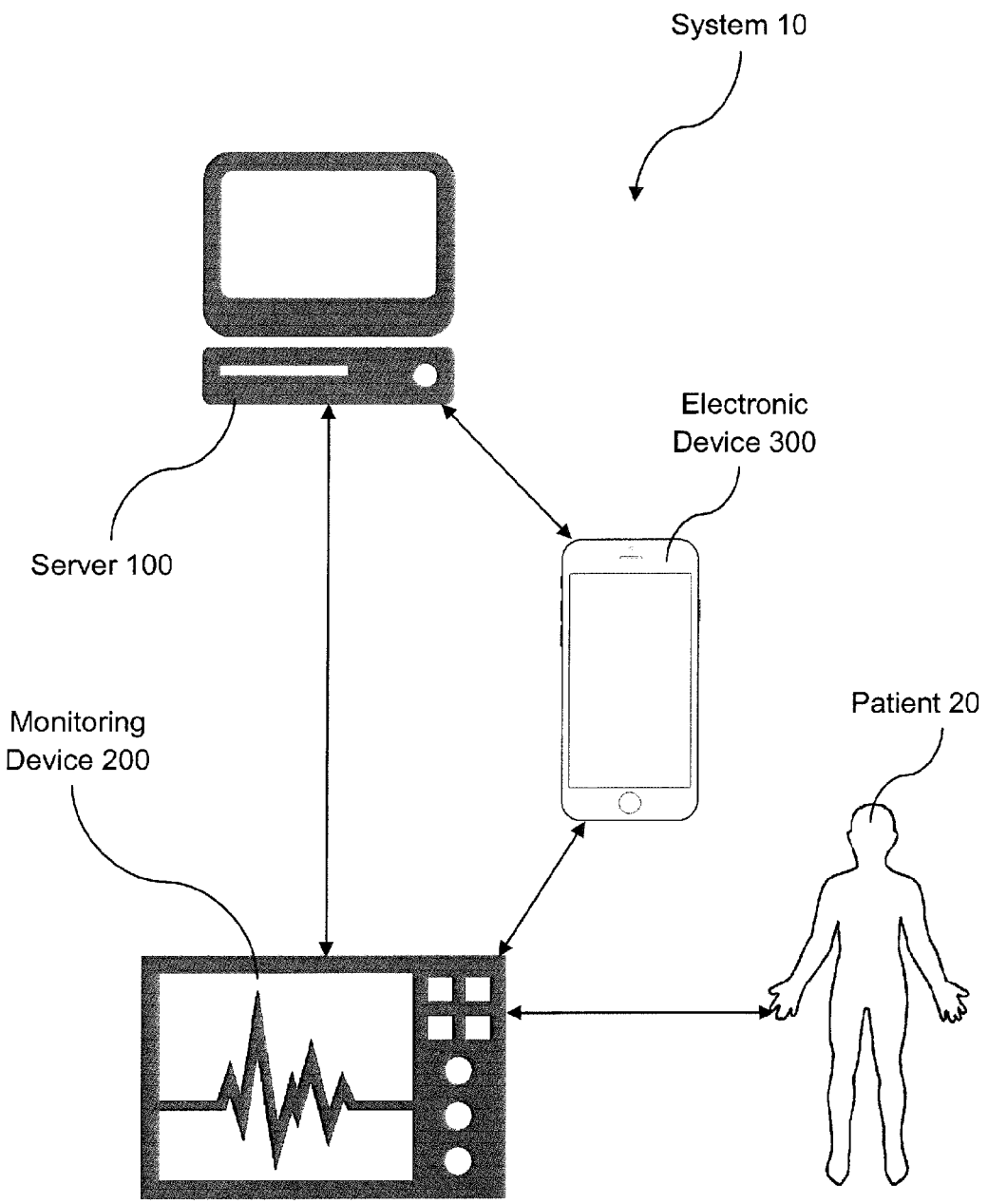
FIG. 1 is an illustration of a system for non-invasively monitoring health of a vascular system of a patient, in accordance with an embodiment of the present disclosure.

In representative or exemplary embodiments of the present disclosure, there is an electronic system 10 as illustrated in FIG. 1. The system 10 includes a host server or server 100 having a processor and a memory configured to store computer-readable instructions. The processor (also referred to as a central processor unit or CPU) is in communication with memory devices including secondary storage (such as disk drives or memory cards), read only memory (ROM), and random access memory (RAM). The processor may be implemented as one or more CPU chips. The processor executes instructions, codes, computer programs, scripts which it accesses from hard disk, floppy disk, optical disk (these various disk based systems may all be considered secondary storage), flash drive, ROM, RAM, or network connectivity devices. The server 100 may include one or multiple processors. Thus, while instructions may be discussed as executed by a processor, the instructions may be executed simultaneously, serially, or otherwise executed by one or multiple processors.

The system 10 further includes a monitoring device 200 connected or connectable to a patient/subject/user 20 and communicatively linked to or communicable with the server 100. The monitoring device 200 is an electronic hardware component/module for measuring vascular activity of the patient 20. The monitoring device 200 includes a set of measuring instruments for obtaining measurements related or derived from the vascular activity, such as volumetric changes resulting from fluctuations in blood flow and electrical activity from cardiac function. The server 100 is cooperative with the monitoring device 200 for performing a method for non-invasively monitoring the vascular system health of the patient 20.

In one embodiment, the monitoring device 200 includes or is integrated with network connectivity devices for communicating with the server 100. The network connectivity devices may take the form of modems, modem banks, Ethernet cards, universal serial bus (USB) interface cards, serial interfaces, token ring cards, fibre distributed data interface (FDDI) cards, wireless communication modules, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other known network devices. These network connectivity devices may enable the monitoring device 200, specifically a processor therein, to communicate with the server 100 via the Internet or one or more intranets.

In another embodiment as shown in FIG. 1, the system 10 includes an electronic device 300 communicatively linked to or communicable with the monitoring device 200 and/or server 100. The electronic device 300 functions as an intermediary device between the server 100 and monitoring device 200, such that the monitoring device 200 is communicable with the server 100 via the electronic device 300. For example, the monitoring device 200 measures the vascular activity of the patient 20 and automatically communicates data derived from these vascular activity measurements to the server 100 via the electronic device 300. Alternatively, the monitoring device 200 may first communicate the data to the electronic device 300 for storage, and the electronic device 300 communicates the data to the server 100 at a later time. This may happen if the patient 20 is being measured by the monitoring device 200 and there is zero or limited network connectivity in the area.

The electronic device 300 includes the network connectivity devices described above for facilitating communication between the server 100 and monitoring device 200. The electronic device 300 may be a mobile device such as a mobile phone, smartphone, personal digital assistant (PDA), tablet, laptop, or computer.

Figure 2:
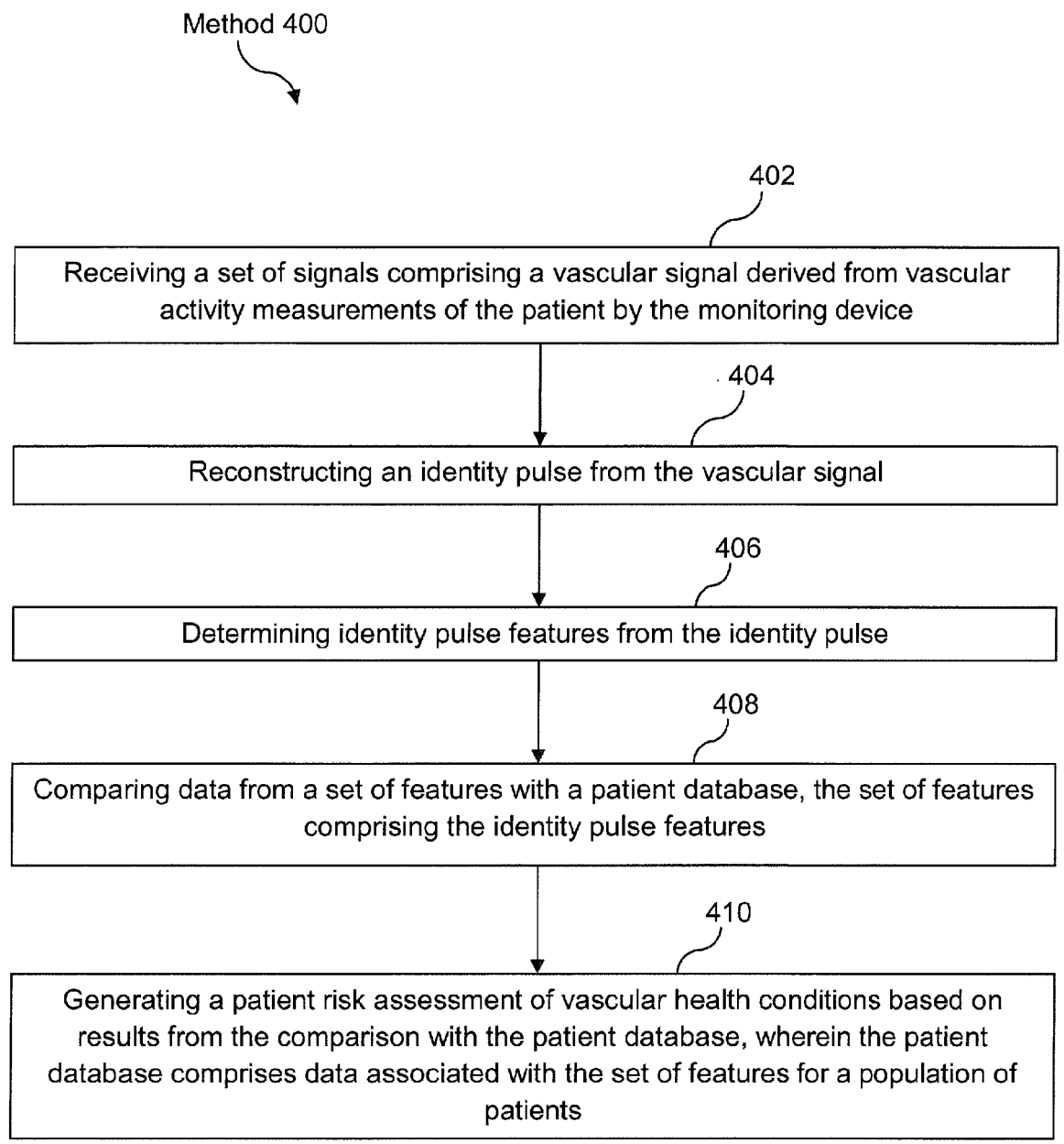
FIG. 2 is an illustration of a computerized method for non-invasively monitoring health of a vascular system of a patient, in accordance with an embodiment of the present disclosure.

In various embodiments of the present disclosure with reference to FIG. 2, there is a computerized method 400 implemented on the server 100 for non-invasively monitoring vascular system health of the patient 20. Broadly, the method 400 includes:

(a) a step 402 of receiving a set of signals comprising a vascular signal derived from vascular activity measurements of the patient by the monitoring device 200;
(b) a step 404 of reconstructing an identity pulse from the vascular signal;
(c) a step 406 of determining identity pulse features from the identity pulse;
(d) a step 408 of comparing data from a set of features with a patient database, the set of features comprising the identity pulse features; and
(e) a step 410 of generating a risk assessment of vascular health conditions based on results from the comparison with the patient database, wherein the patient database comprises data associated with the set of features for a population of patients.

Figure 3:
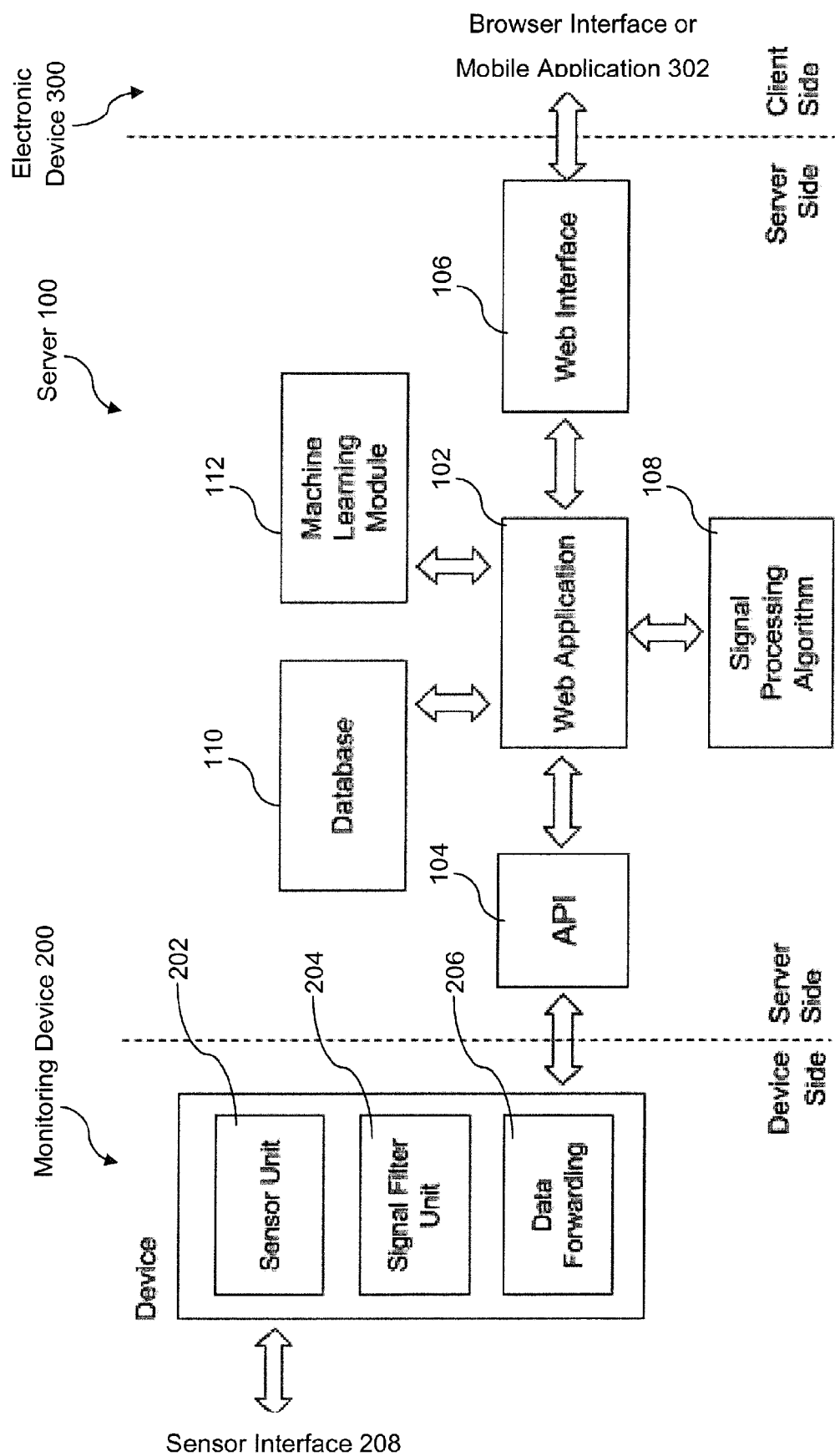
FIG. 3 is a block diagram illustration of a server of the system of FIG. 1, in accordance with an embodiment of the present disclosure.

Referring to FIG. 3, the server 100 (server side) includes a software module for performing the method 400. The software module includes an application or controller 102 for data analysis/interpretation. The application 102 implements an application programming interface (API) 104, a user interface 106 (e.g. web-based or through a mobile application), a signal processing component/module/unit algorithm 108 for processing the set of signals, the patient database 110, and machine learning component/module/unit 112 for comparing data from the set of features with the patient database 110.

The monitoring device 200 (device side) includes a sensor component/module/unit 202, a signal filtering component/module/unit 204, and a data forwarding component/module/unit 206. The set of measuring instruments of the monitoring device 200 interfaces with the monitoring device 200, specifically with the sensor component 202, via a sensor interface 208. The sensor component 202 receives via the sensor interface 202 measurements obtained by the measuring instruments, and generates a set of signals derived from the measurements. In one embodiment, the measurements obtained by the measuring instruments are in the form of analog signals. The monitoring device 200 processes the analog signals with the signal filtering component 204, e.g. converting the analog signals to digital signals, before communicating the digital signals to the server 100 from the data forwarding component 206.

The communication from the monitoring device 200 to the server 100 occurs through the API 104 implemented in the application 102 of the server 100. Once data including the set of signals (digital signals) is communicated to and received by the application 102, the set of signals is processed by the signal processing component 108 and the set of features is determined. Data from set of features including the identity pulse features are stored in the patient database 110 for comparison by the machine learning component 112. After storing the data, the set of features are classified and the patient risk assessment of vascular health conditions is generated using the machine learning module 112, such as by calculating probability scores or values associated with such risks. The vascular health conditions may be related to some vascular anomaly or some cardiovascular disease and the probability scores or values may indicate risks of the patient 20 having or being diagnosed such disease conditions. When these risks are assessed for individuals who are not diagnosed with such diseases, then the probability scores or values may indicate future tendency of having such diseases, thereby giving predictive insights to the patient 20.

The patient risk assessment for vascular health conditions is shown to the patient 20 (client side). In one embodiment, the patient risk assessment is communicated to the electronic device 300 and presented to the patient 20 on a graphical user interface (GUI) 302, e.g. web browser or mobile application executed on the electronic device 300. In another embodiment, the monitoring device 200 includes a graphical user interface on which the patient 20 can directly view the patient risk assessment. The patient risk assessment may be presented to the patient 20 in a visual or graphic format such that they can be readily understood by the patient 20.

It will be appreciated that communications between the server 100, monitoring device 200, and electronic device 300 may occur via wired connections or via wireless communication protocols. The communications may be secured by protocols such as Hypertext Transfer Protocol Secure (HTTPS) and/or implemented with network security systems such as computing firewalls, as will be readily understood by the skilled person.

Figure 4:
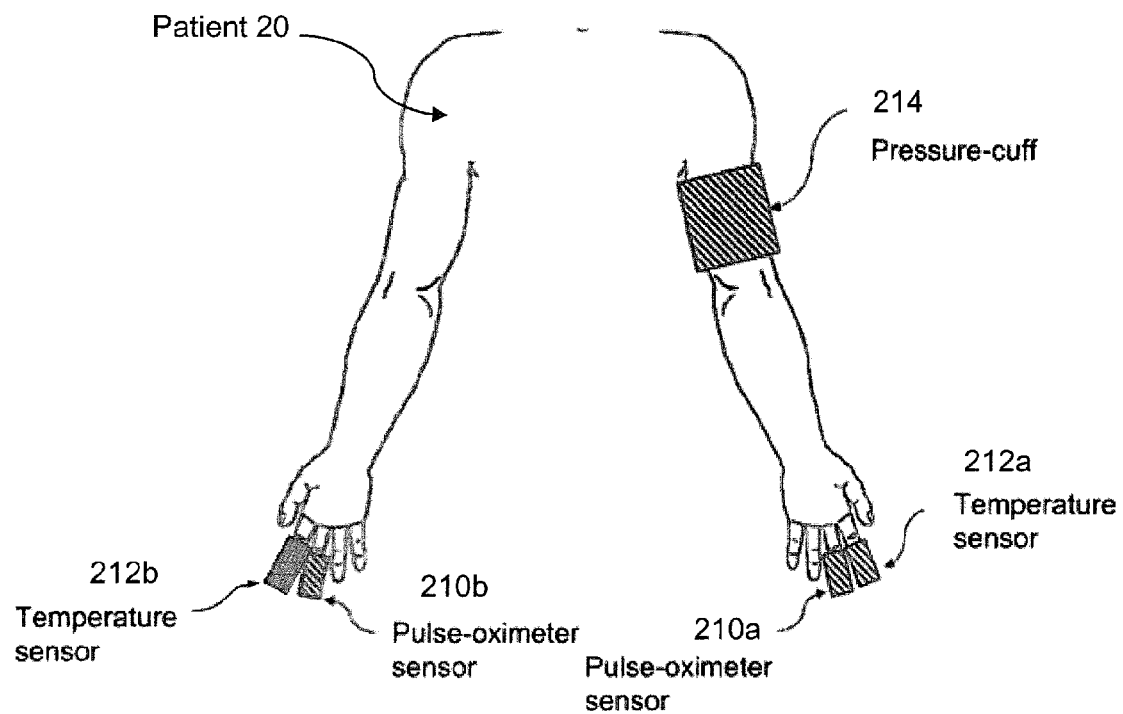
FIG. 4 is an illustration of a configuration of sensors on the patient for non-invasively monitoring the patient's vascular system health, in accordance with an embodiment of the present disclosure.

In one embodiment with reference to FIG. 4, the set of measuring instruments of the monitoring device 200 includes pulse oximeter sensors 210 for measuring vascular activity in the body, temperature sensors 212 for measuring body temperature, and a pressure cuff 214 for causing vascular occlusion attached to the patient 20. Specifically, the pulse oximeter sensors 210 and temperature sensors 212 are attached to extremities or digits of the patient 20, and the pressure cuff 214 is wrapped around the left upper arm. A first pulse oximeter sensor 210a is attached to the left middle finger and a second pulse oximeter sensor 210b is attached to the right middle finger. A first temperature sensor 212a is attached to the left index finger and a second temperature sensor 212b is attached to the right index finger.

In each cardiac cycle, the heart pumps blood to the periphery (e.g. digits) of the body through a pressure pulse. The pressure pulse is sufficient to distend the blood vessels in the subcutaneous tissue in the body skin, thereby changing the blood volume of the subcutaneous tissue in the body skin. A pulse oximeter sensor 210 is a vascular sensor that measures vascular activity (i.e. resulting from blood circulation) in the body. Specifically, the pulse oximeter sensor 210 measures the amount of oxygen in blood indirectly by determining the oxygen saturation level ($SO_2$) of the haemoglobin in blood and also measures changes in blood volume in the body skin. The change in volume caused by the pressure pulse can be detected by illuminating the skin with the light from a light-emitting diode (LED) and then measuring the amount of light either transmitted or reflected to a photodiode. A pulse oximeter sensor 210 is attached to a digit to illuminate the skin and measure changes in light absorption. The measured changes in light absorption collectively produce a photoplethysmogram (PPG).

The monitoring device 200 begins taking measurements of the patient 20 when the patient 20 at rest in a comfortable position. Preferably, the patient 20 should avoid drugs or alcohol for at least 4 hours before the measurements as they could affect vascular activity. After an initial resting period, e.g. 30 minutes, measurements from the multiple pulse oximeter sensors 210 and temperature sensors 212 are continually taken for a predefined time period, e.g. 2 minutes. Alternatively, this initial resting period may be omitted. The pressure cuff 214 is then inflated to a predefined pressure, e.g. 50 mmHg or 6.7 kPa, above the systolic blood pressure. The pressure cuff 214 is maintained in the inflated state for a predefined time period, e.g. 3 minutes, after which the same measurements are taken. The pressure cuff 214 is then deflated or released and the same measurements are taken for another predefined time period, e.g. 5 minutes. Measurements obtained from the right arm (without the pressure cuff 214) may be referred to as a baseline or reference.

Accordingly, this procedure obtains measurements of the patient 20 before and after artificially stimulating the vascular endothelium. The vascular endothelium is stimulated by restricting the blood flow to the left arm using the pressure cuff 214 and causing the vascular endothelium to release nitric oxide. Using this configuration of multiple pulse oximeter sensors 210 and temperature sensors 212, more accurate measurements can be obtained since there are two sets of measurements—one wherein the vascular endothelium is at rest and the other wherein the vascular endothelium is stimulated. However, there are some disadvantages in that it is time consuming to perform this measurement procedure and the inflation of the pressure cuff 214 may be uncomfortable to the patient 20. Furthermore, it may not be suitable or not recommended by doctors to subject some patients to vascular occlusion (e.g. blockage or restriction of blood flow in the arm) by the pressure cuff 214, especially if they have certain conditions or diseases.

Figure 5:
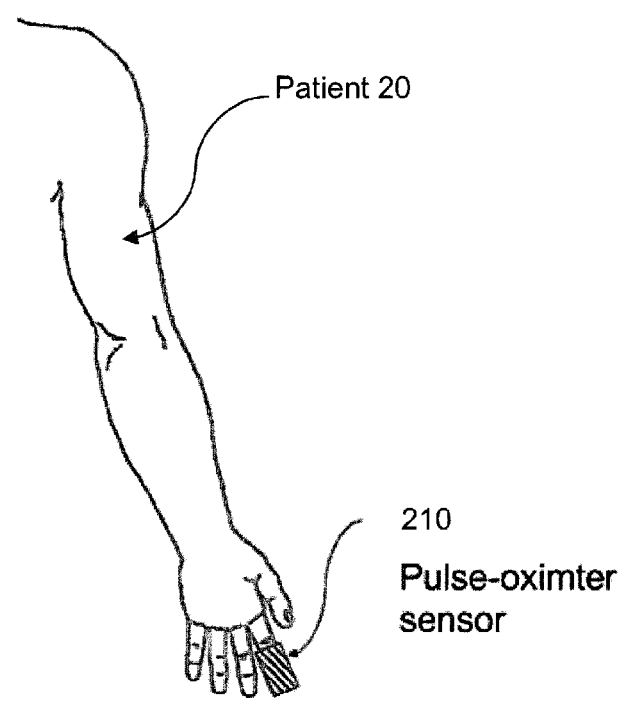
FIG. 5 is an illustration of another configuration of sensors on the patient for non-invasively monitoring the patient's vascular system health, in accordance with another embodiment of the present disclosure.

In another embodiment with reference to FIG. 5, the set of measuring instruments of the monitoring device 200 includes a pulse oximeter sensor 210 attached to the left index finger of the patient 20. Similarly, the monitoring device 200 begins taking measurements of the patient 20 when the patient 20 at rest in a comfortable position. After an initial resting period, e.g. 30 minutes, measurements from the pulse oximeter sensor 210 are continually taken for a predefined time period, e.g. 3 minutes. Alternatively, this initial resting period may be omitted. While the measurements may be less accurate than those from the previous embodiment in FIG. 4, this procedure is more convenient to use and more comfortable to the patient 20 as it is not necessary for the vascular endothelium to be artificially stimulated.

In yet another embodiment, the set of measuring instruments of the monitoring device 200 includes electrocardiogram (ECG) sensors or electrodes placed on the skin and near the heart of the patient 20. The set of measuring instruments may optionally include one or more temperature sensors 212. Similarly, the monitoring device 200 begins taking measurements of the patient 20 when the patient 20 at rest in a comfortable position. After an initial resting period, e.g. 30 minutes, measurements from the ECG sensors are continually taken for a predefined time period, e.g. 10 minutes. The ECG sensors measure and record the heart's electrical activity and produce an ECG. The ECG may be used to assess the cardiac system or function of the patient 20 and the risk of cardiac dysfunction.

It will be appreciated that various types of vascular sensors other than the pulse oximeter sensors 210 and ECG sensors may be implemented or used on the patient 20 to measure vascular activity or obtain bodily measurements/readings related to vascular activity. Consequently, various types of signals may be produced by such vascular sensors other than PPG and ECG, such as other forms of plethysmograms, as will be readily understood by the skilled person.

In various embodiments, the set of measuring instruments of the monitoring device 200 obtains various measurements from the patient 20, such as vascular activity measurements by the pulse oximeter sensors 210, temperature measurements by the temperature sensors 212, and electrical activity measurements by the ECG sensors or electrodes. The measurements are measured as analog signals that are communicated to the monitoring device 200 via the sensor interface 208. The signal filtering component 204 of the monitoring device 200 processes the analog signals before the data forwarding component 206 communicates to the server 100 for further processing.

Figure 6:
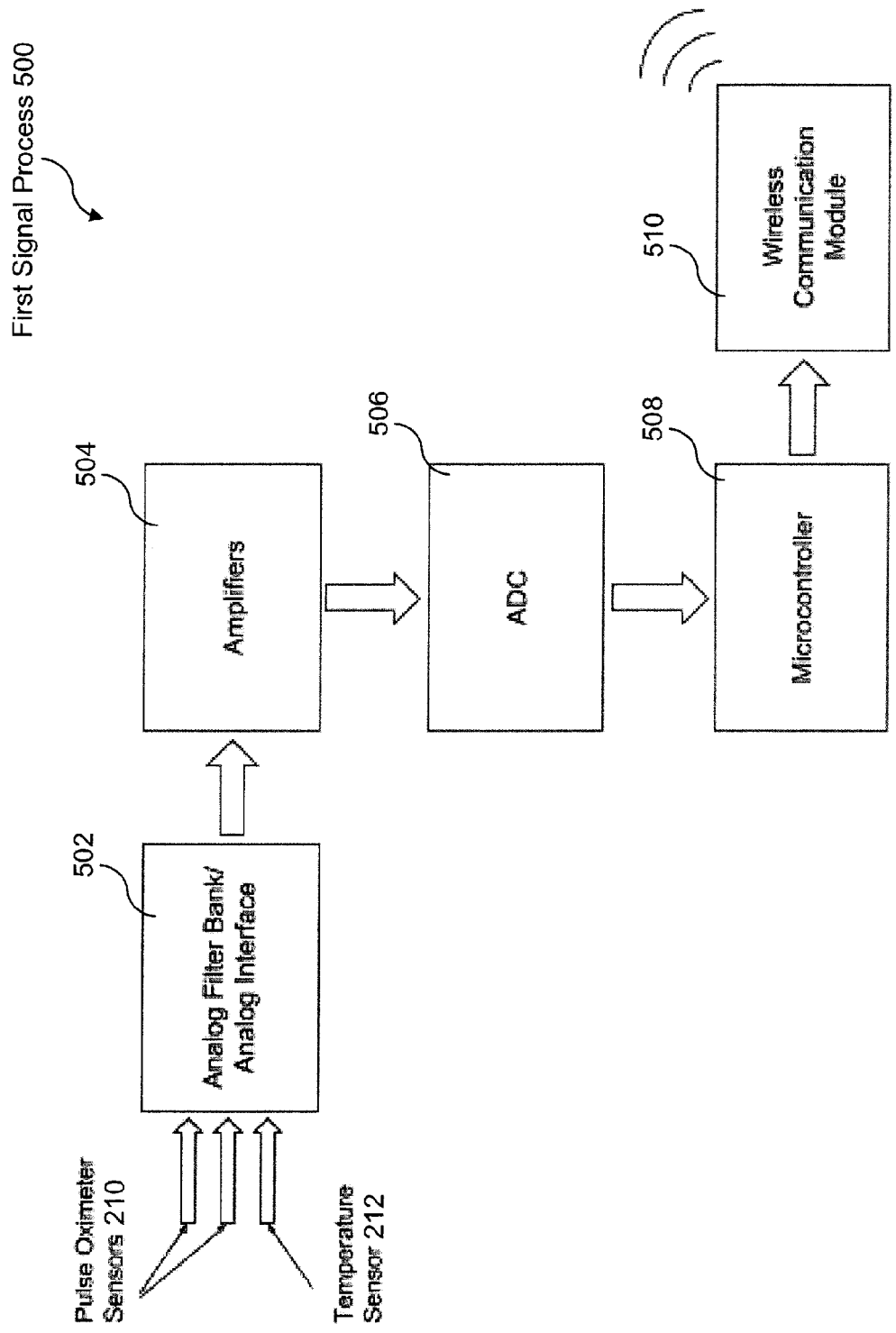
FIG. 6 is an illustration of a first signal process performed on photoplethysmogram (PPG) and temperature signals, in accordance with an embodiment of the present disclosure.

In one embodiment with reference to FIG. 6, the analog signals include two vascular signals derived from the pulse oximeter sensors 210 and one temperature or thermal signal derived from the temperature sensor 212. Each analog signal is processed by the signal filtering component 204 of the monitoring device 200 in a first signal process 500. The analog signals are first filtered by an analog filter bank/analog interface 502 and then amplified by one or more amplifiers 504. The filtered and amplified analog signals are converted into the digital domain by an analog-to-digital converter (ADC) 506. Basically, the ADC 506 converts the analog signals (refined by the filtering and amplifying steps) into digital signals. A microcontroller 508 then formats the digital signals in order to communicate them by the data forwarding module 206, e.g. including a wireless communications module 510, to the server 100. Accordingly, the monitoring device 200 generates a set of digital signals and communicates the digital signals to the server 100 for further processing.

Figure 7:
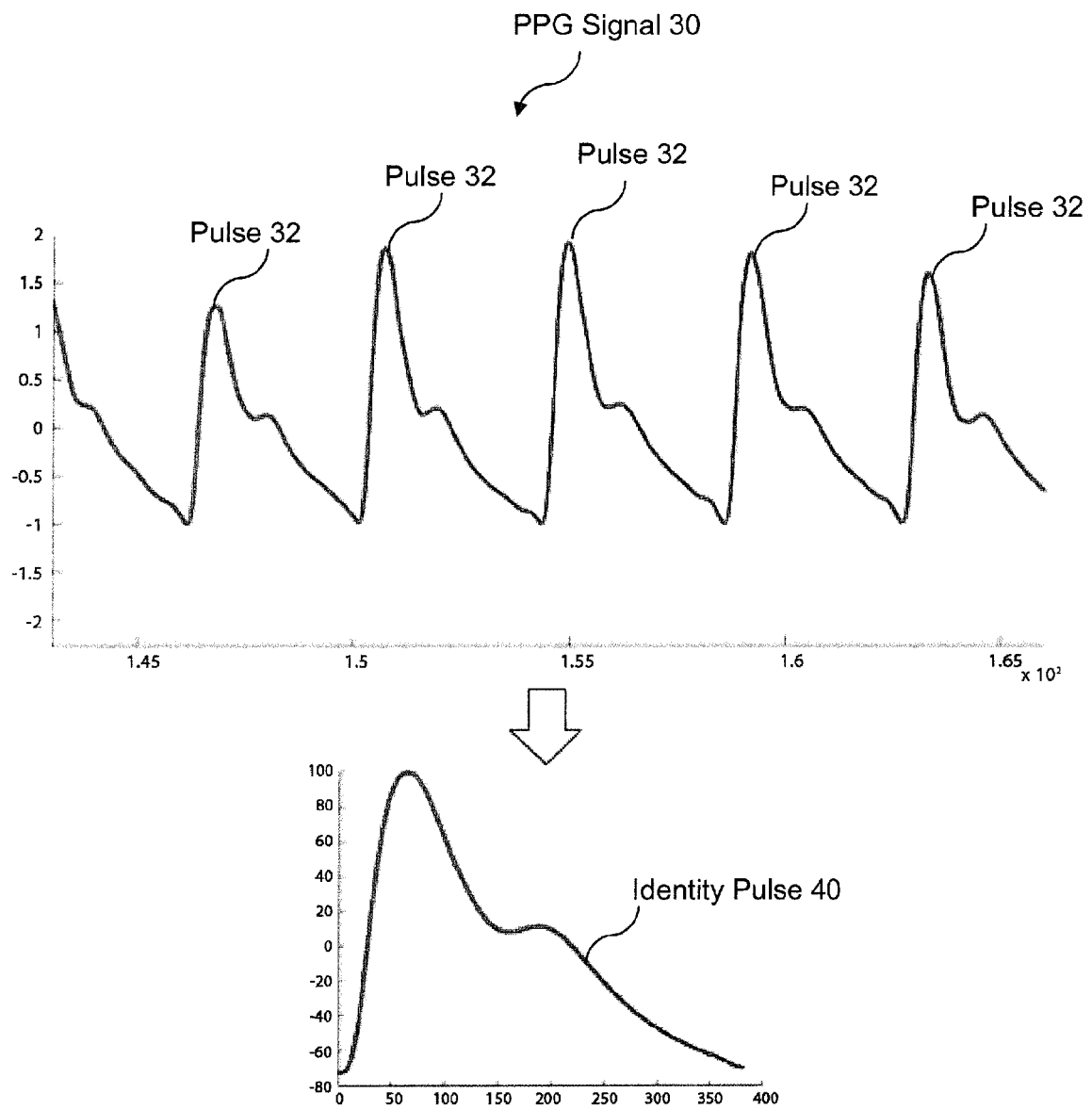
FIG. 7 is an illustration of reconstructing an identity pulse from the PPG signal after a second signal process, in accordance with an embodiment of the present disclosure.

In one embodiment with a sensor configuration as shown in FIG. 5, the set of signals, e.g. digital signals resulting from the first signal process 500, includes a vascular signal derived from vascular activity measured by the pulse oximeter sensor 210. As the vascular signal is derived from a PPG produced by the pulse oximeter sensor 210, the vascular signal may be referred to as a PPG signal. The set of signals including the PPG signal is received by the server 100 in the step 402 of the method 400. With reference to FIG. 7, the PPG signal 30 is in the time domain as the vascular activity measurements are taken across various time periods. In the step 404, an identity pulse 40 is reconstructed from the PPG signal 30. The identity pulse 40 is reconstructed from the PPG signal 30 after signal processing as described below. In signals or signal processing, a "pulse" is defined as a rapid transient change in a characteristic, e.g. amplitude, phase, or frequency, of a signal from a baseline/reference value to a higher or lower value, followed by a rapid return to the baseline/reference value. To illustrate simplistically, the PPG signal 30 shown in FIG. 7 is a pulse train/wave (pulse amplitude modulated signal) with a series/sequence of discrete pulses 32. Although the identity pulse 40 may appear similar to one of the discrete pulses 32, the identity pulse 40 is derived from processing the entire series of discrete pulses 32 in the pulse train/wave of the PPG signal 30 into a single resulting pulse, instead of simply extracting a single discrete pulse 32 from the PPG signal 30. It will be appreciated that the identity pulse 40 / a discrete pulse 32 may include small/minute subsidiary pulses or subpulses that may be insignificant to the overall profile or shape of the identity pulse 40 / discrete pulse 32. In the step 406, identity pulse features can be determined or extracted from the identity pulse 40 for assessing risks of vascular health conditions of the patient 20.

Figure 8:
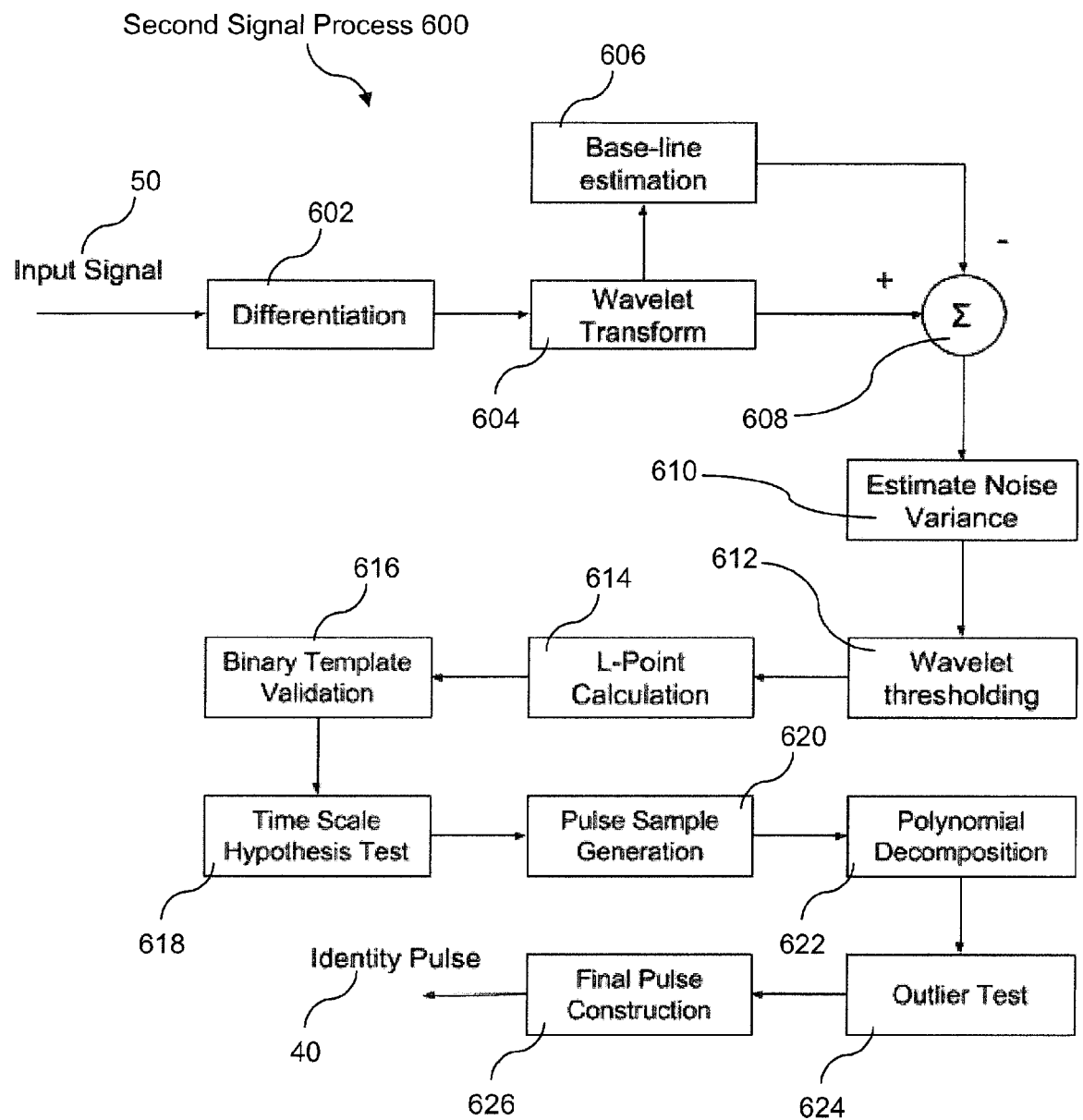
FIG. 8 is an illustration of the second signal process, in accordance with an embodiment of the present disclosure.

The server 100, specifically the signal processing component 108 thereof, may process the vascular signal received in the step 402 for reconstructing the identity pulse 40 in the step 404. With reference to FIG. 8, a second signal process 600 is performed on the vascular signal by the signal processing component 108 of the server 100. The vascular signal is received by the signal processing component 108 as a digital input signal 50. The input signal 50 is analyzed in different resolutions to identify the high resolution components, low resolution components, and the original signal component as a baseline or reference.

Figure 9:
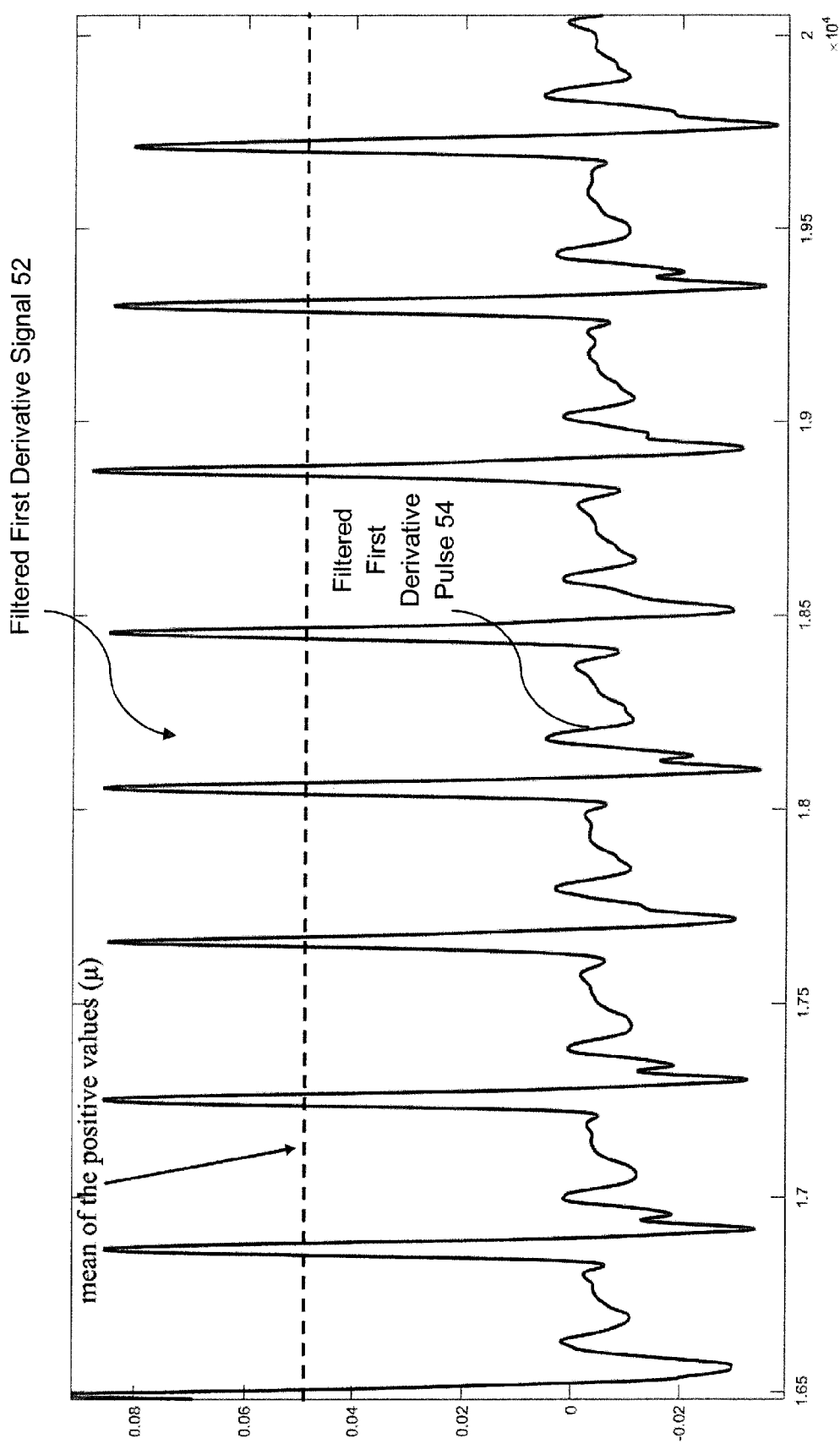
FIG. 9 is an illustration of a first derivative of the PPG signal, in accordance with an embodiment of the present disclosure.

In a step 602 of the second signal process 600, the input signal 50 is differentiated to obtain a first derivative signal therefrom. In a step 604, a wavelet transform or wavelet-based multi-resolution analysis is used to analyze the input signal 50. Operations of the wavelet-based multi-resolution analysis are performed on the first derivative signal as there are strong correlations with the Daubechies wavelets family. The first derivative signal is analyzed based on the Daubechies wavelets family, e.g. decomposition of wavelets in the first derivative signal, for feature localization and identification of the high, mid-range, and low resolution components. The high resolution components are representative of the Gaussian noise. The low resolution components are representative of random motion artifacts, noise from sensor couplings, and other low level noises. The mid-range resolution components are representative of the desired components of the first derivative signal, which may be predefined through experimentations. The baseline or reference from the original first derivative signal may be estimated or constructed by numerical integration in a step 606 to facilitate identification of the mid-range resolution components. In a step 608, the low resolution components are combined to generate a resultant of all low resolution components or low frequency artifacts, and are subsequently subtracted out from the first derivative signal. Among the resulting components of the wavelet-transformed first derivative signal, the high resolution components are used to estimate the noise variance in a step 610. The noise variance is used to filter the first derivative signal and subtract out the noise components embedded in the input signal 50 using a wavelet thresholding based denoising technique in a step 612, e.g. VisuShrink technique. The steps 602, 604, 606, 608, 610, and 612 may be collectively referred to as the initial filtering phases to obtain a resulting signal that is filtered from noise. The resulting signal may be referred to as filtered first derivative signal 52. An illustration of the filtered first derivative signal 52 from the input signal 50 is shown in FIG. 9. As the filtered first derivative signal 52 is derived from the input signal 50 which is the PPG signal 30, the filtered first derivative signal 52 may alternatively be referred to as the first derivative of the filtered PPG signal 30.

Subsequently, a step 614 known as "L-Point Calculation" is performed on the filtered first derivative signal 52 shown in FIG. 9 to isolate substantially undistorted pulses from the pulse train/wave thereof. The filtered first derivative signal 52 shows dominance in the positive side (dominance in the amplitude), and the primary peak is significantly larger than the secondary peak. Thus, as shown in FIG. 9, the mean of the positive values ($\mu$) lies between the two major maxima of the filtered first derivative signal 52. Peaks added to the original first derivative signal 52 due to noise (e.g. in the low resolution components) cannot cause a large shift in $\mu$. Therefore, the mean p of the positive values of the filtered first derivative signal 52 can be used as a threshold for locating the vicinity of the systolic peak. The step 614 locates the points in the filtered first derivative signal 52 that exceed $\mu$ (threshold points) and traces back to the nearest zero point in the filtered first derivative signal 52 that occurred before the threshold point, which is then marked as a "possible starting point" of a pulse 54 of the filtered first derivative signal 52.

Figure 10:
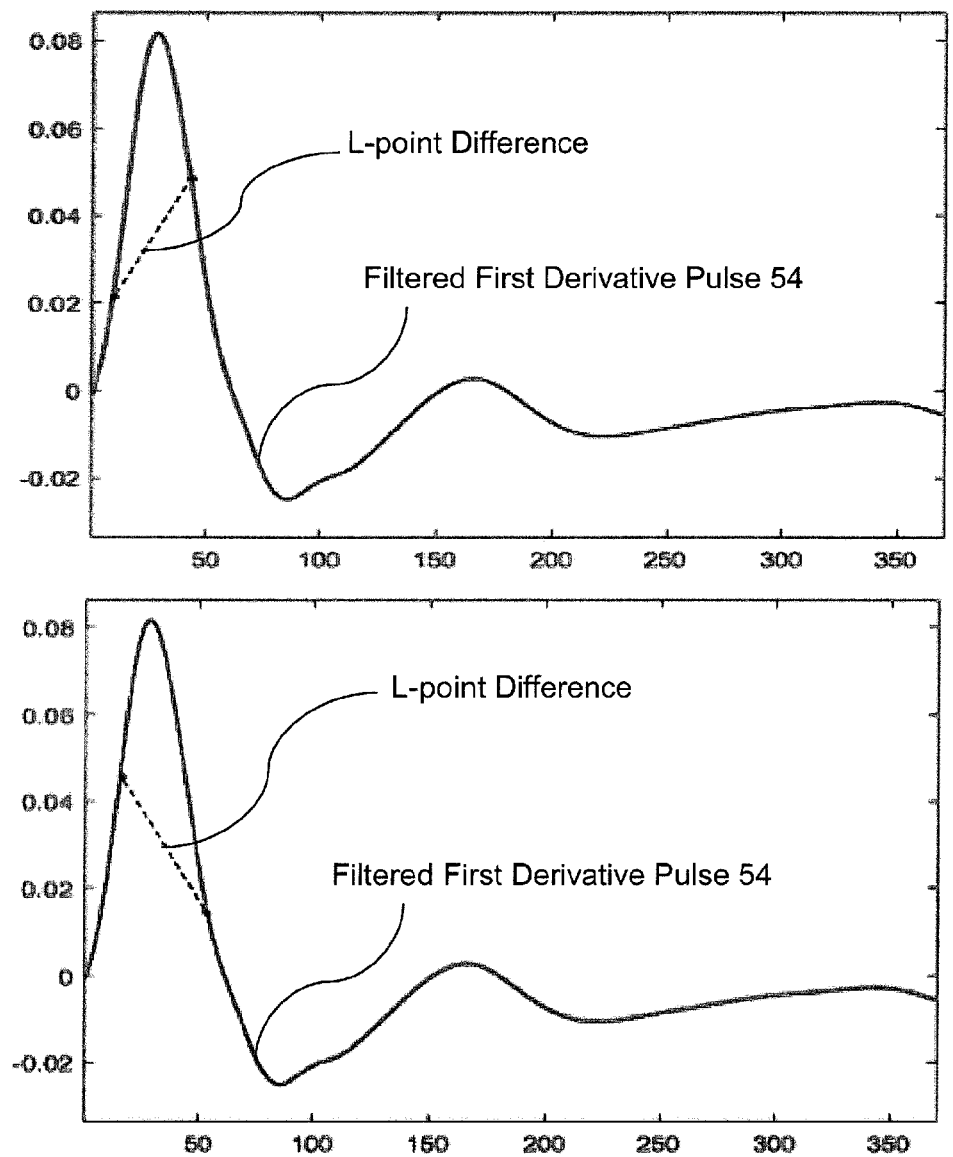
FIG. 10 is an illustration of example pulses from the first derivative of the PPG signal of FIG. 9, in accordance with an embodiment of the present disclosure.

A "possible pulse 54" of the filtered first derivative signal 52 may be defined as being between two consecutive "possible starting points". FIG. 10 illustrates examples of a possible pulse 54 from the filtered first derivative signal 52, or otherwise referred to as the filtered first derivative pulse 54. To increase the probability that two consecutive "possible starting points" can yield a "possible pulse 54", an "L-point difference" is first defined as the difference between points in the filtered first derivative signal 52 located L samples apart, according to the equation below. For each filtered first derivative pulse 54 illustrated in FIG. 10, the dotted line defines the "L-point difference" between two "possible starting points" located L samples apart.

$$L\text{-point Difference} = (\text{Filtered first derivative signal } 52)(n+L) - (\text{Filtered first derivative signal } 52)(n),$$

where n is some sample and L is the step.

The step 614 computes the L-point difference along the filtered first derivative signal 52 shown in FIG. 9 and identifies the points where its sign changes, which yields a sequence or pattern of sign changes. In a step 616, this pattern of sign changes can be matched against a predefined pattern or template in order to check whether the expected ripples are present in the filtered first derivative signal 52 and in the correct order. Notably, the predefined template is a binary sign changing pattern, meaning that the values it contains—is defined with a positive "+" sign or a negative "−" sign. Experimental data indicates that the sign change pattern [+,−,+,−,+,−,+,−,+] yields optimal results. "Possible starting points" in the form of the filtered first derivative signal 52 that do not follow this pattern of sign changes in the L-point difference are rejected or excluded.

The L-point difference can capture the important ripples in the filtered first derivative signal 52 without being adversely affected by noise unlike a first or second order difference. Accordingly, the offset L should not exceed the length of the shortest ripple otherwise the L-point difference would not be able to capture that ripple. Assuming the shortest ripple is symmetric, half its length is a suitable value for L, according the equation below.

$$L = 0.5 * r * \text{floor}[(\text{length of the longest ripple})],$$

where r is the mean ratio between the lengths of the shortest and longest ripples in the filtered first derivative signal 52 which was found to be 0.25 in a typical PPG signal.

Since the probability distribution of noise is a decaying function of noise magnitude (e.g. Gaussian noise), the correct value of L makes the L-point difference a robust mechanism to detect ripples in the filtered first derivative signal 52.

The template matching technique described in the step 616 removes some of the "possible starting points" of pulses in the pulse train/wave of the filtered first derivative signal 52 identified earlier by systolic peak detection. Consequently, the distribution of lengths between two consecutive "possible starting points" becomes dispersed, as shown in FIG. 10. Furthermore, exceptionally longer and shorter lengths in this distribution represent pulses that should be rejected or excluded. In a step 618, a statistical test, e.g. a time scale hypothesis test, is performed. Specifically, the statistical test is performed on the hypothesis that two consecutive "possible starting points" mark the two ends of a "possible pulse".

Figure 11:
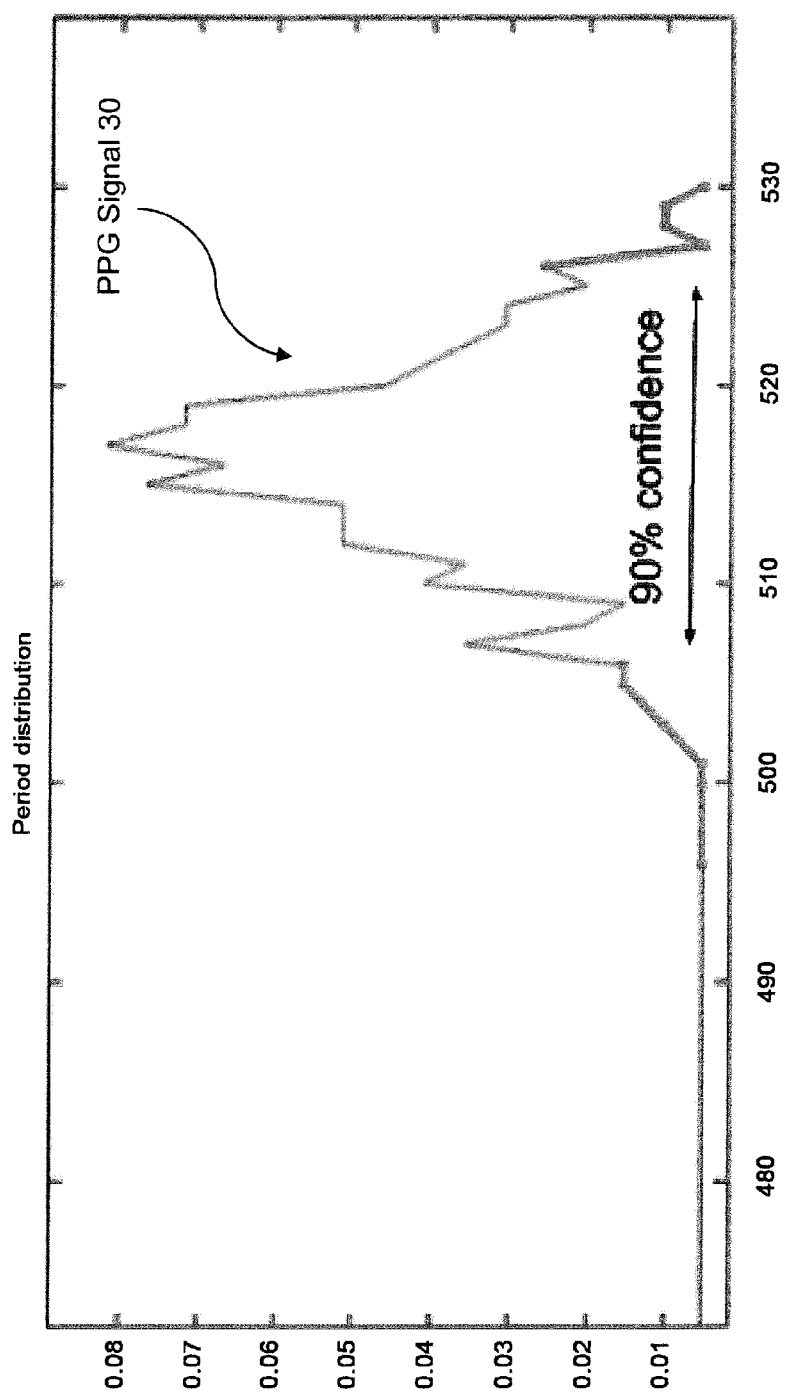
FIG. 11 is an illustration of the PPG signal with a predefined confidence interval, in accordance with an embodiment of the present disclosure.

To test the hypothesis, a probability distribution of lengths of "possible pulses" is constructed. With reference to FIG. 11 which illustrates the probability distribution with Gaussian behavior, pulses with lengths falling outside a predefined confidence interval, e.g. a 90% confidence interval, are rejected or excluded. In this manner, the "possible end point" of a pulse can be indirectly identified. Implementing another constraint on this probability distribution that takes into account the relative positions of systolic and diastolic peaks can further eliminate distorted pulses. The systolic peak in a desired pulse occurs before the diastolic peak and has larger amplitude, as illustrated in the filtered first derivative signal 52 in FIG. 9. The relative positions of systolic and diastolic peaks correspond to the ripple pattern in the filtered first derivative signal 52. Therefore, the amplitudes of the three maxima in the filtered first derivative signal 52 must be in descending order. The L-point difference on the filtered first derivative signal 52 is used to locate the maxima and calculate their amplitudes. Pulses that do not conform to this criterion of predefined descending order of amplitudes are rejected or excluded.

Therefore, the pulses in the filtered first derivative signal 52 are further validated and the resulting set of pulses are further filtered by considering the range starting from the "possible starting points" that are identified in the step 614 to the "possible end points" that are validated through the statistical test in the step 618. In a step 620, a first set of sample pulses is consequently generated as a result of the aforementioned steps performed on the filtered first derivative signal 52.

The first set of sample pulses may still have undesired distortions which are present within the shape of the pulses' curves. In a step 622, a polynomial decomposition is performed on the sample pulses in order to eliminate such distorted pulses. For example, an orthogonal family of polynomials may be used for the polynomial decomposition of all the pulses in the first set of sample pulses. Specifically, Chebyshev polynomials of the first kind, which is a set of orthogonal polynomials defined as the solutions to the Chebyshev differential equation, within the range (−1, 1) may be used for the polynomial decomposition. The coefficients are grouped by the index of the coefficient resulting in a set of coefficients ($C_n$) for all the pulses in the first set of sample pulses for some given coefficient index n, wherein 0<n<25. This means that $C_n$, for some n, contains coefficients of all the pulses in the first set of sample pulses. By considering the variance for each $C_n$, coefficients with maximum sensitivity to the shape distortions are derived.

In a step 624, the coefficients with maximum sensitivity to the distortions are tested for outliers. Each coefficient $C_n$ is tested separately. Outlier coefficients in a group for some $C_n$ correspond to the pulses with some anomalies in their shapes with respect to majority of the pulses. An example of the outlier test used for detecting one or more outliers is the "Generalized Extreme Studentized Deviate (ESD) Test for Outliers". Pulses that fail the outlier test, i.e. outlier pulses, are rejected or excluded. A second set of sample pulses is consequently generated by excluding pulses which fail at the outlier test for any $C_n$ which is considered for the outlier test.

In a final step 626 of the second signal process 600, the pulses in the second set of sample pulses are superimposed and integrated into a single pulse. The single pulse may then be normalized to thereby reconstruct the identity pulse 40. The normalization of the single pulse may be within the range [0, 1] in the amplitude scale and/or time scale to remove or mitigate the effects of heart rate variation. The identity pulse 40 is thus reconstructed from the original PPG signal 30 in the step 404 of the method 400 by performing the second signal process 600 thereon. In the step 406 of the method 400, identity pulse features are determined or extracted from the identity pulse 40. In the step 408, data from a set of features including these identity pulse features is compared by the machine learning component 112 with the patient database 110. Consequently, in the step 410, the machine learning component 112 generates a risk assessment of vascular health conditions of the patient 20.

Therefore, the second signal process 600 is performed for reconstruction of the identity pulse 40 from the input signal 50/PPG signal 30. It will be appreciated that one or more of the steps in the second signal process 600 performed on the PPG signal 30, or in some steps on the filtered first derivative signal 52, may be selectively omitted or excluded. For example, some of the steps may be performed on a first derivative of the PPG signal 30 which has not been filtered. Furthermore, while the second signal process 600 has been described above in relation to a single PPG signal 30, it will be appreciated that aspects of the second signal process 600 may be applicable to multiple PPG signals or vascular signals in general. For example, multiple vascular signals of the same type, e.g. multiple PPG signals, may be superimposed/integrated/averaged together to subsequently reconstruct the identity pulse 40 and determine identity pulse features therefrom.

Data from the set of features (also known as indices) including the identity pulse features from the identity pulse 40 can be compared to the patient database 110 to obtain predictive results on vascular health conditions of the patient 20. In addition, data from the set of features associated with the patient 20 can be updated into the patient database 110, thereby including the patient 20 into the patient population inside the patient database 110. The inclusion of new data into the patient database 20 facilitates training of and learning by the machine learning component 112. Furthermore, the patient population may be classified based on their vascular health status. For example, some patients 20 may have vascular health conditions which can be detected by standard medical tests, while other patients 20 may have vascular health conditions in the early stages which cannot be detected by standard medical tests.

Figure 12:
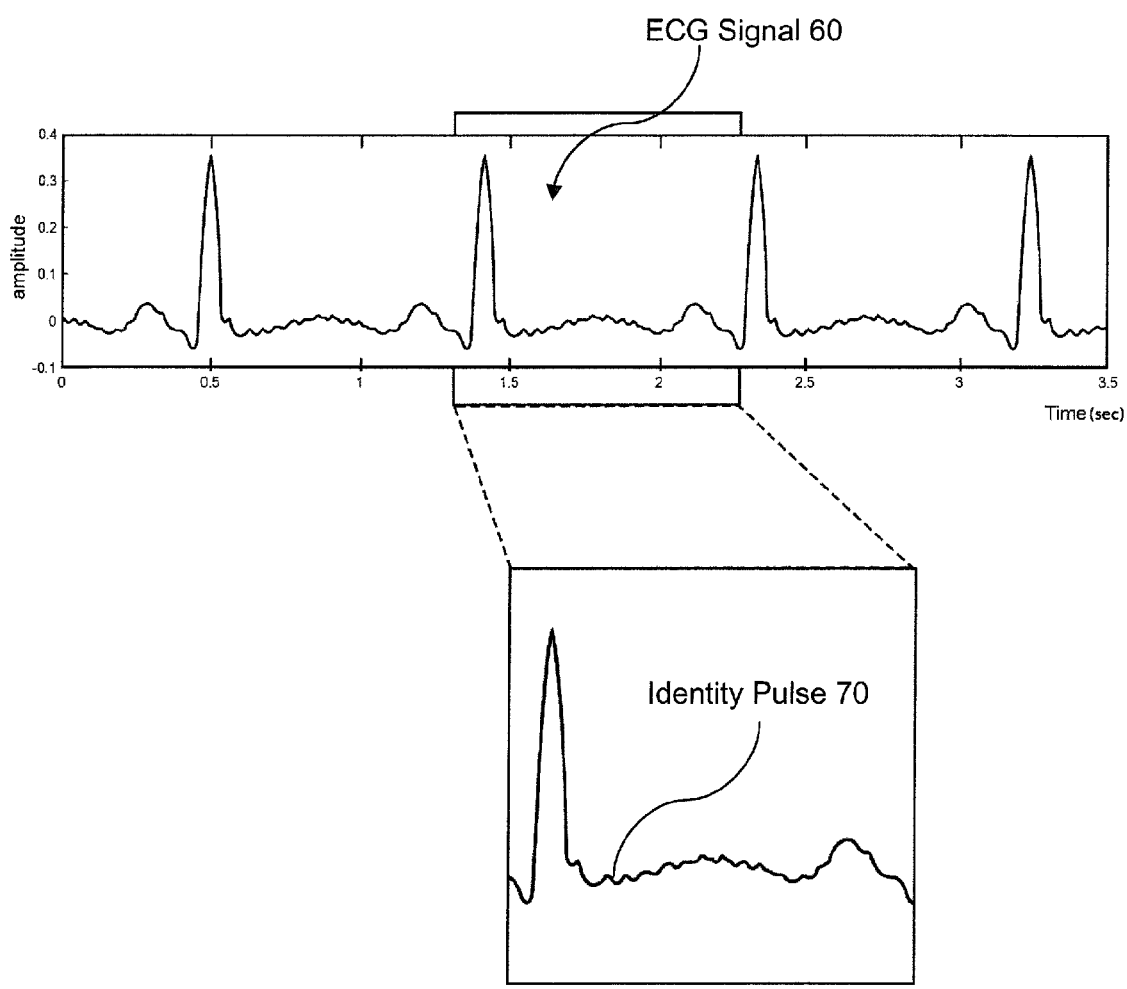
FIG. 12 is another illustration of reconstructing an identity pulse from an electrocardiogram signal, in accordance with another embodiment of the present disclosure.

In another embodiment, the set of signals resulting from the first signal process 500 includes a vascular signal derived from electrical activity measured by the ECG sensors/electrodes. The vascular signal may thus be referred to as an ECG signal. An example of an ECG signal 60 in the time domain is shown in FIG. 12. Similar to the PPG signal 30 described above, an identity pulse 70 can be reconstructed from the ECG signal 60 because the first derivatives of the PPG signal 30 and ECG signal 60 have similarity in patterns. Identity pulse features are similarly determined or extracted from the identity pulse 70 to assess/evaluate/calculate risks of vascular health conditions, particularly cardiac dysfunction, and thereby generate a patient risk assessment. The machine learning component 112 can be similarly trained by including data from the identity pulse features of the identity pulse 70 into the patient database 20, as well as classifying the patient population into different cardiac function categories.

In some embodiments, each patient 20 in the patient database 110 are identified by their personal parameters, such as age and gender. In the step 410, the patient risk assessment may be generated based additionally on the comparison of data from the personal parameters with the patient database 110. The personal parameters facilitate better classification of the patient population, such as into various age groups, particularly because elderly patients 20 are more susceptible to vascular diseases.

In one embodiment, the patient 20 inputs the personal parameters directly on the monitoring device 200. In another embodiment, the patient 20 inputs the personal parameters on an application executed on the electronic device 300. A questionnaire or survey with a set of questions may be prompted or presented to the patient 20 to answer and complete. The electronic device 300 thus captures the personal parameters and communicates them to the server 100 for training the machine learning component 112, improving the accuracy of results and classifications for different groups of patients 20. The personal parameters that are captured from the patient 20 include, but are not limited to the followings list.

List of Personal Parameters
1. Name
2. Date of Birth
3. Gender
4. Height
5. Weight
6. Waist Circumference
7. Country/Region/Geographical Area
8. Known vascular diseases, comorbidities, and family history of vascular diseases (e.g. diabetes mellitus, hypertension or high blood pressure, stroke, high cholesterol, chronic kidney disease, ischemic heart disease, heart attacks, chest pains, etc.)
9. Habits that would affect vascular health (e.g. smoking, alcohol consumption, etc.)
10. Last known or measured blood pressure level (systolic and diastolic)
11. Last known or measured cholesterol level
12. Last known or measured blood sugar level Notably, personal parameters such as the blood pressure, cholesterol, and blood sugar levels may not be known to the patient 20. These personal parameters may be omitted from input or may alternatively be measured by appropriate medical instruments connected to the monitoring device 200 and/or electronic device 300.

The machine learning component 112 relies on the set of features or indices, including identity pulse features determined from the identity pulse 40, the personal parameters input by the patient 20, and optionally temperature signal features from a temperature signal (e.g. rate of rise of temperature). Data from the set of features may be used for assessing risks of vascular health conditions of the patient 20, i.e. a diagnosis mode or process, and/or use for training the machine learning component 112, i.e. a training mode or process. It will be appreciated that not all the features share the same significance; each feature may be weighted differently depending on its significance. Various analytical and/or statistical methods may be used to assess/estimate the importance or level of significance of each feature, and consequently assess correlations towards endothelial function and vascular health conditions/diseases.

Broadly, some of these methods include:
1. Correlation coefficient and coefficient of determination
2. Receiver operating characteristic (ROC) curve analysis of single feature classifiers
3. Optimal feature subset selection
4. Summation of variations of mean squared error The machine learning component 112 uses a trained Support Vector Machine (SVM) model/structure with a non-linear or quadratic kernel function, or a similar trained machine learning data structure, for generating the comparison results and patient risk assessment/evaluation. In the training mode or process, different SVM models are trained depending on the personal parameters input by the patient 20. After the training and classification of the SVM models for a given set of features, the probability scores or values associated with such risks are calculated to determine the likelihood of the set of features belonging to the group which resulted from the SVM classification. For this purpose, the length of resultant of the vectors of the set of features from the classification hyperplane in the SVM model is taken into consideration. The probability value for a given length of the resultant feature vector is assigned by the Platt scaling or calibration algorithm.

The machine learning component 112 is continuously trained for different groups in the population of patients 20 by introducing more training data obtained from the patients 20. The machine learning component 112 can adaptively optimize its classification using the set of features derived from the training data set for each group or sub-population. Once the features, including those derived from signals fed from a patient 20 as well as the personal parameters input by the patient, are obtained, the machine learning component 112 is capable of comparing the features against the group or sub-population that are best matched to the given features. Consequently, the probability scores or values are calculated for various vascular health conditions, anomalies, and/or diseases, and a patient risk assessment is thereby generated.

In one embodiment, the sensor configuration as shown in FIG. 4 is used. The monitoring device 200 receives a first analog vascular signal and a first analog temperature signal derived from the first pulse oximeter sensor 210a and first temperature sensor 212a, respectively, attached to the left arm (stimulated by pressure cuff 214). The monitoring device 200 additionally receives a second analog vascular signal and a second analog temperature signal derived from the second pulse oximeter sensor 210b and second temperature sensor 212b, respectively, attached to the right arm (at rest). The analog signals are processed in the first signal process 500, and a resultant digital vascular signal and a resultant digital temperature signal are communicated to the server 100 for further processing.

Improved accuracy of the results can be gained through the application of the features determined or extracted from the vascular and temperature signals. In one embodiment, the vascular signal is a PPG signal 30 as shown in FIG. 7. Specifically, FIG. 7 illustrates the PPG signal 30 in the time domain or time spectrum as well as the identity pulse 40 that has been reconstructed from the PPG signal 30 in the step 404 and after performing the second signal process 600.

Figure 13:
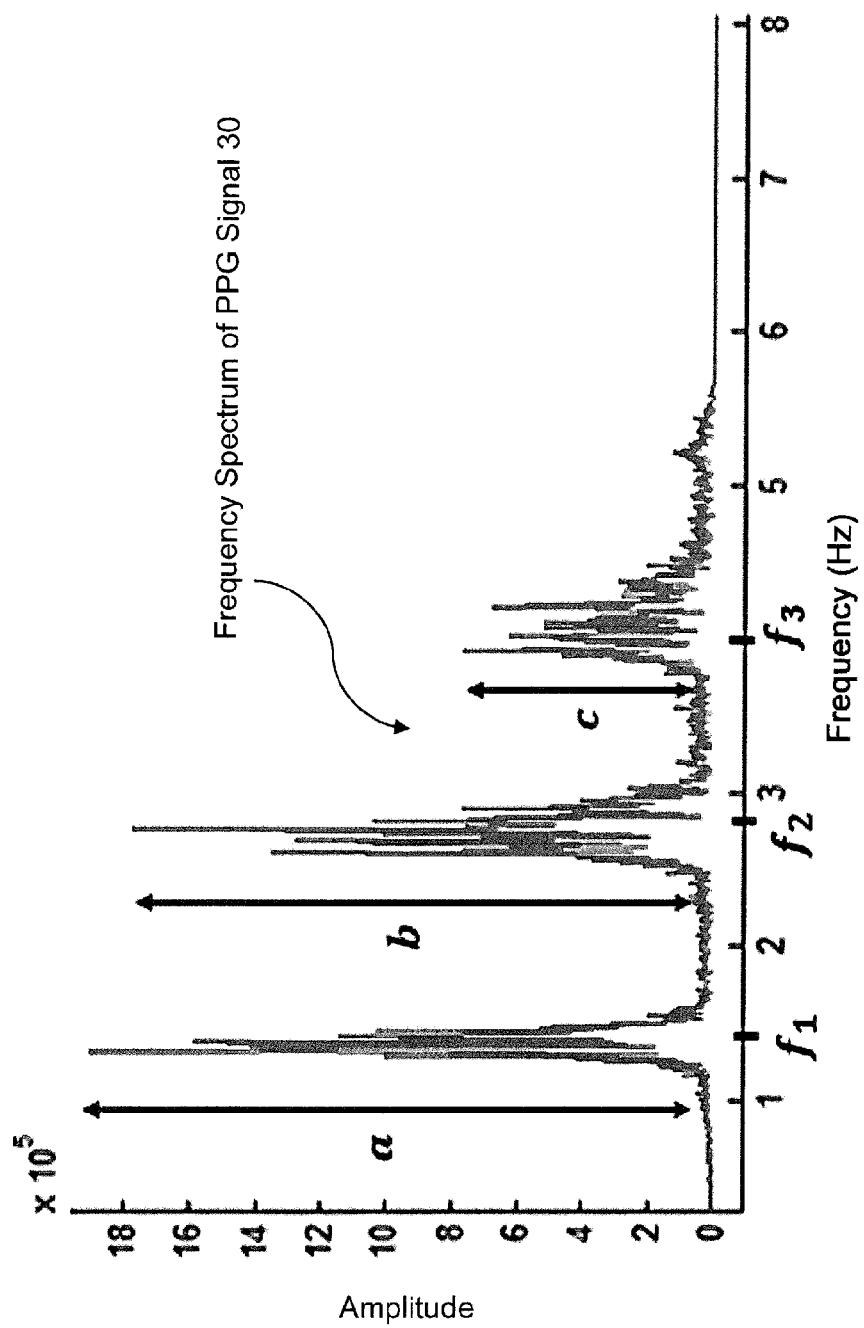
FIG. 13 is an illustration of the PPG signal in the frequency domain, in accordance with an embodiment of the present disclosure.
Figure 14:
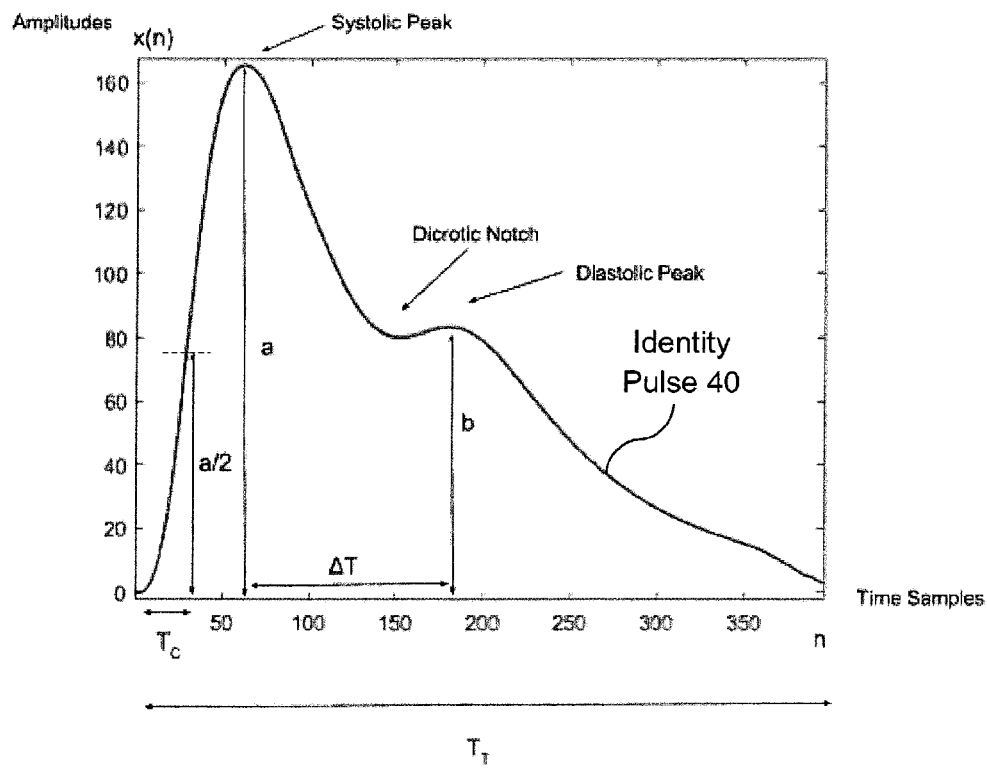
FIG. 14 is an illustration of an identity pulse derived from the PPG signal, in accordance with an embodiment of the present disclosure.
Figure 15:
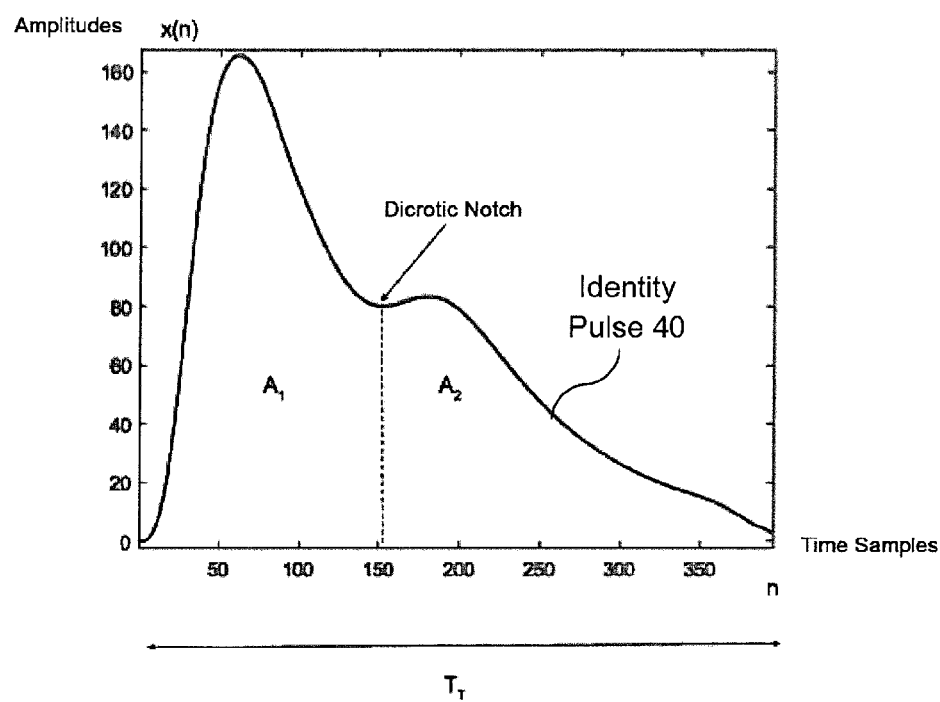
FIG. 15 is another illustration of the identity pulse of FIG. 13, in accordance with an embodiment of the present disclosure.
Figure 16:
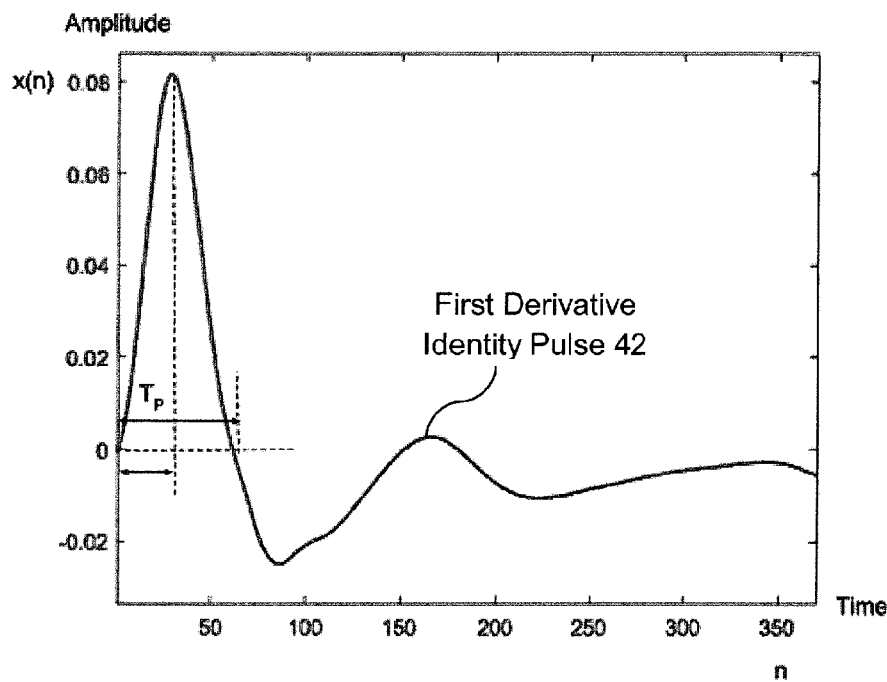
FIG. 16 is an illustration of a first derivative of the identity pulse of FIG. 13, in accordance with an embodiment of the present disclosure.
Figure 17:
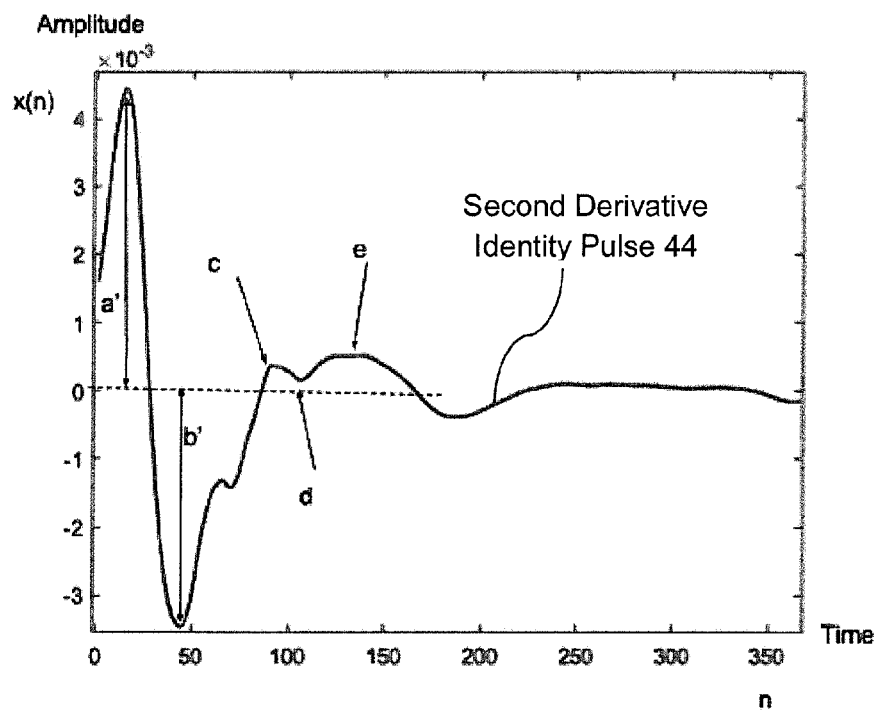
FIG. 17 is an illustration of a second derivative of the identity pulse of FIG. 13, in accordance with an embodiment of the present disclosure.
Figure 18:
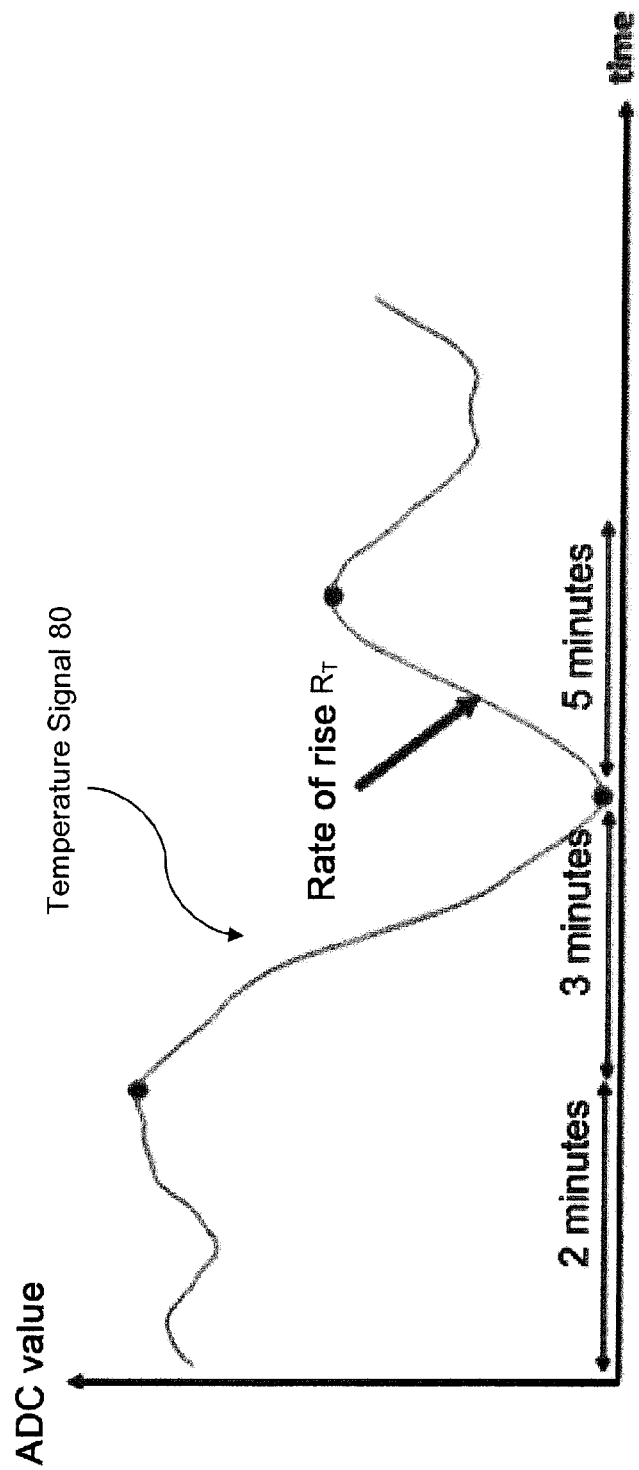
FIG. 18 is an illustration of the temperature signal, in accordance with an embodiment of the present disclosure.

FIG. 13 illustrates a representation of the PPG signal 30 in the frequency spectrum or frequency domain. FIG. 14 and FIG. 15 illustrate the identity pulse 40 reconstructed from the PPG signal 30 in the time domain. FIG. 16 illustrates a first derivative of the identity pulse 40 in the time domain, i.e. the first derivative identity pulse 42. FIG. 17 illustrates a second derivative of the identity pulse 40 in the time domain, i.e. the second derivative identity pulse 44. FIG. 18 illustrates the temperature signal 80 in the time domain obtained during the period of inflation and deflation of the pressure cuff 214, as derived from the temperature sensors 212 in the sensor configuration as shown in FIG. 4.

The features determined from the identity pulse 40, first derivative identity pulse 42, second derivative identity pulse 44, frequency spectrum of PPG signal 30, and/or temperature signal 80 provide accurate estimation for assessing/evaluating/calculating risk of various vascular health conditions/diseases. Some non-limiting examples of the features are listed in Table 1 below. Definitions of symbols used in the features are shown in Table 2 below.

TABLE 1

| Feature | Definition | Illustration |
|---|---|---|
| Reflection Index | $= \dfrac{a}{b}$ | FIG. 14 |
| Stiffness Index | $= \dfrac{l}{\Delta T}$ | FIG. 14 |
| Area Under Curve | $= \sum_n x(n)$ | FIG. 14 |
| Pulse Width | $= T_P$ | FIG. 16 |
| Crest Time | $= T_C$ | FIG. 14 |
| Peak to Peak Interval (Heart Rate) | $= T_T$ | FIG. 14 |
| Der2-1 Index (First Curvature Point Ratio) | $= \dfrac{b'}{a'}$ | FIG. 17 |
| Der2-2 Index | $= \dfrac{d}{a'}$ | FIG. 17 |
| Der2-3 Index | $= \dfrac{b' - c - d}{a'}$ | FIG. 17 |
| Der2-4 Index (Ageing Index) | $= \dfrac{b' - c - d - e}{a'}$ | FIG. 17 |
| Der2-5 Index | $= \dfrac{b' - c - d - e}{b'}$ | FIG. 17 |
| Der3-6 Index | $= \dfrac{b' - e}{a'}$ | FIG. 17 |
| Der3-7 Index | $= \dfrac{c}{a'}$ | FIG. 17 |
| Inflection Point Area Ratio | $= \dfrac{A_2}{A_1}$ | FIG. 15 |
| Frequency Related to the First Peak in the Frequency Domain | $= f_1$ | FIG. 13 |
| Frequency Related to the Second Peak in the Frequency Domain | $= f_2$ | FIG. 13 |
| Frequency Related to the Third Peak in the Frequency Domain | $= f_3$ | FIG. 13 |
| Sum of the Amplitudes of the First Three Peaks in the Frequency Domain | $= a + b + c$ | FIG. 13 |
| Rate of Rise of Temperature | $= R_T$ | FIG. 18 |

TABLE 2

| Symbol | Definition |
|---|---|
| a | Systolic peak |
| b | Diastolic peak |
| $\Delta T$ | Time difference between systolic and diastolic peaks |
| n | Time sample |
| x(n) | Digital sample values for time sample n |
| $T_P$ | Length of the first peak in the first derivative identity pulse 42 |
| $T_C$ | Time duration from the beginning to half of the maximum value of the identity pulse 40 (at the rising side) |
| $T_T$ | Total width of the identity pulse 40 |
| b' | First minima of the second derivative identity pulse 44 |
| a' | First maxima of the second derivative identity pulse 44 |
| c | Second maxima (after the major slope of passing b') of the second derivative identity pulse 44 |
| d | First minima after c of the second derivative identity pulse 44 |
| e | First maxima after d of the second derivative identity pulse 44 |
| $A_1$ | Area under the curve of the identity pulse 40 at the left side of the Dicrotic notch |
| $A_2$ | Area under the curve of the identity pulse 40 at the right side of the Dicrotic notch |

The machine learning component 112 thus uses one or more of the aforementioned features to assess/evaluate/calculate risks of various vascular health conditions, anomalies, and/or diseases which the patient 20 may currently have or may contract in future. From this global set of features, smaller sets or more optimum sets of features may be derived to better perform the risk assessment for certain conditions/diseases and generate a concise patient risk assessment. The optimums set of features are analytically determined using the previously stored training data, as well as considering the importance/significance of the features. The optimum feature sets for different conditions/diseases are shown in Table 3 below.

TABLE 3

| Condition/Disease | Feature |
|---|---|
| Diabetes | Sum of the Amplitudes of the First Three Peaks in the Frequency Domain |
| | Peak to Peak Interval (Heart Rate) |
| | Der2-2 Index |
| | Der2-3 Index |
| | Rate of Rise of Temperature |
| Hypertension/High Blood Pressure | Sum of the Amplitudes of the First Three Peaks in the Frequency Domain |
| | Peak to Peak Interval (Heart Rate) |
| | Der2-3 Index |
| | Der2-4 Index (Ageing Index) |
| | Der2-5 Index |
| | Rate of Rise of Temperature |
| Heart Attacks | Reflection Index |
| | Crest Time |
| | Stiffness Index |
| | Der3-6 Index |
| | Rate of Rise of Temperature |
| High Cholesterol | Der2-1 Index (First Curvature Point Ratio) |
| | Der2-2 Index |
| | Der2-3 Index |
| | Rate of Rise of Temperature |
| Chronic Kidney Disease | Der3-7 Index |
| | Der2-4 Index (Ageing Index) |
| | Rate of Rise of Temperature |

The system 10 and method 400 disclosed herein provides an improved approach for non-invasively monitoring health of a vascular system of a patient 20. The server 100 of the system 10 uses a machine learning component 112 to obtain a vascular signal and optionally a temperature signal from the patient 20 and processes the vascular signal to reconstruct an identity pulse. Identity features and temperature signal features from the identity pulse and temperature signal, respectively, are determined and data from these features are compared with a patient database 110. Results of the comparison are used to generate a patient risk assessment of vascular health conditions, such as by calculating a probability score on whether the patient 20 has a condition/disease or whether the patient 20 is likely to contract some condition/disease in future.

The use of an identity pulse provides a more standardized approach which patients, clinics, medical facilities, etc. can adopt for making comparisons and assessing risks of vascular health conditions. Compared to a conventional signal or pulse train, a single identity pulse derived in substantially the same manner for different patients can more effectively emphasize the variations between patients depending on their vascular health, resulting in better accuracy in detecting vascular health conditions/anomalies/diseases. Data from the features, together with appropriate personal parameters of the patient 20, may also be used to update the patient database 110 (which has records of a population of patients) and to train the machine learning component 112, thereby improving the accuracy in detecting/predicting vascular health conditions/anomalies/diseases.

In the foregoing detailed description, embodiments of the present disclosure in relation to a system and method for non-invasively monitoring health of a vascular system are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A system for non-invasively monitoring health of a vascular system of a patient, the system comprising:
   a monitoring device for measuring vascular activity of the patient; and
   a server configured for performing steps comprising:
      receiving a set of signals comprising a vascular signal derived from vascular activity measurements of the patient by said monitoring device;
      performing a signal process on the vascular signal, the signal process comprising:
         differentiating the vascular signal to obtain a first derivative signal;
         finding local maxima of the first derivative signal;
         determining pulses in the first derivative signal wherein the local maxima of the pulses do not conform to a predefined descending order of amplitudes; and
         excluding the determined pulses from the vascular signal;
      reconstructing an identity pulse from the processed vascular signal;
      determining identity pulse features from the identity pulse;
      comparing data from a set of features with a patient database, the set of features comprising the identity pulse features; and
      generating a patient risk assessment of vascular health conditions based on results from the comparison with the patient database, wherein the patient database comprises data associated with the set of features for a population of patients.

2. The system according to claim 1, wherein the signal process comprises superimposing pulses in the vascular signal into a single pulse.

3. The system according to claim 2, wherein the signal process comprises normalizing the single pulse to thereby reconstruct the identity pulse.

4. The system according to claim 1, further comprising:
   a set of measuring instruments connectable to said monitoring device, wherein said set of measuring instruments comprise one or more vascular sensors for measuring the vascular activity of the patient.

5. The system according to claim 4, the measuring instruments further comprising one or more temperature sensors for measuring temperature of the patient, wherein the set of signals further comprises a temperature signal derived from temperature measurements of the patient, the steps further comprising determining temperature signal features from the temperature signal, wherein the set of features further comprises the temperature signal features.

6. The system according to claim 4, wherein the vascular signal is derived from a plethysmogram or an electrocardiogram resulting from the vascular activity measurements, the vascular sensors comprising a pulse oximeter sensor or an electrocardiogram sensor for obtaining the plethysmogram or electrocardiogram, respectively.

7. A computerized method implemented on a server for non-invasively monitoring health of a vascular system of a patient, the method comprising:
   receiving a set of signals comprising a vascular signal derived from vascular activity measurements of the patient by a monitoring device;
   performing a signal process on the vascular signal, the signal process comprising:
      differentiating the vascular signal to obtain a first derivative signal;
      finding local maxima of the of the first derivative signal;
      determining pulses in the first derivative signal where the local maxima of the pulses do not conform to a predefined descending order of amplitudes; and
      excluding the determined pulses from the vascular signal;
   reconstructing an identity pulse from the processed vascular signal;
   determining identity pulse features from the identity pulse;
   comparing data from a set of features with a patient database, the set of features comprising the identity pulse features; and
   generating a patient risk assessment of vascular health conditions based on results from the comparison with the patient database, wherein the patient database comprises data associated with the set of features for a population of patients.

8. The method according to claim 7, wherein the signal process comprises filtering the vascular signal from noise.

9. The method according to claim 8, wherein the signal process comprises excluding pulses falling outside a predefined confidence interval from the vascular signal.

10. The method according to claim 9, wherein the signal process comprises performing a polynomial decomposition on the vascular signal.

11. The method according to claim 10, wherein the signal process comprises excluding outlier pulses from the vascular signal.

12. The method according to claim 11, wherein the signal process comprises superimposing pulses in the vascular signal into a single pulse.

13. The method according to claim 12, wherein the signal process comprises normalizing the single pulse to thereby reconstruct the identity pulse.

14. The method according to claim 7, further comprising comparing data from personal parameters of the patient with the patient database, wherein the personal parameters are input by the patient and communicated from an electronic device.

15. The method according to claim 14, wherein the patient risk assessment is generated based additionally on the comparison of data from the personal parameters with the patient database.

16. The method according to claim 14, further comprising updating the patient database with data from the set of features and personal parameters associated with the patient.

17. The method according to claim 7, wherein the patient risk assessment comprises a probability of the patient contracting a vascular condition.

* * * * *